US010744024B2

(12) United States Patent
Senyei et al.

(10) Patent No.: US 10,744,024 B2
(45) Date of Patent: Aug. 18, 2020

(54) TRACTION APPARATUS AND METHODS

(71) Applicant: OHANA ALANA, LLC, Solana Beach, CA (US)

(72) Inventors: Andrew Senyei, La Jolla, CA (US); M. Lou Marsh, Del Mar, CA (US); Stuart L. Gallant, San Diego, CA (US); Stuart Karten, Venice, CA (US); Michael Jacob Rocha, Playa del Rey, CA (US); Steven K. Piorek, Los Angeles, CA (US); Eric Olson, Los Angeles, CA (US); Paul Cash, Los Angeles, CA (US)

(73) Assignee: OHANA ALANA, LLC, Solana Beach, CA (US)

( * ) Notice: Subject to any disclaimer, the term of this patent is extended or adjusted under 35 U.S.C. 154(b) by 627 days.

(21) Appl. No.: 14/563,864

(22) Filed: Dec. 8, 2014

(65) Prior Publication Data

US 2015/0157487 A1 Jun. 11, 2015

Related U.S. Application Data

(62) Division of application No. 12/069,134, filed on Feb. 6, 2008, now Pat. No. 8,905,958.

(51) Int. Cl.
*A61F 5/00* (2006.01)
*A61F 5/048* (2006.01)
*A61F 5/055* (2006.01)

(52) U.S. Cl.
CPC .............. *A61F 5/048* (2013.01); *A61F 5/055* (2013.01)

(58) Field of Classification Search
CPC .. A61F 5/048; A61F 5/055; A61F 5/04; A61F 5/042
See application file for complete search history.

(56) References Cited

U.S. PATENT DOCUMENTS

| | | |
|---|---|---|
| 2,102,069 A | 12/1937 | Hanicke |
| 2,706,982 A | 4/1955 | Hale et al. |
| 2,736,314 A | 2/1956 | Hale |
| 2,791,999 A | 5/1957 | Bustamante |
| 2,807,260 A | 9/1957 | Teufel |
| 2,820,455 A | 1/1958 | Hall |
| 2,885,234 A | 5/1959 | Larson |

(Continued)

*Primary Examiner* — Victoria J Hicks
(74) *Attorney, Agent, or Firm* — Gazdzinski & Associates, PC

(57) ABSTRACT

A brace and traction device and associated methods of operation. In one embodiment, the device incorporates a forwardly open head and jaw brace which is adjustably supported vertically above a forwardly collar member. The brace and the collar member are adapted such that the brace is able to mate with the collar member while still being able to rotate to the subject's left and right while remaining planar to the collar member. Adjustment may be accomplished for example manually or via an electronic motor controlled by a control mechanism and microprocessor. The microprocessor may be adapted to store information regarding a user's sessions, and facilitate communication with patient and physician personal devices, thus sending these data from recorded sessions. The processor element may also be adapted to implement therapy sessions based on physician-entered program specifications, or based on preprogrammed specifications.

6 Claims, 12 Drawing Sheets

(56) References Cited

U.S. PATENT DOCUMENTS

| | | |
|---|---|---|
| 3,177,869 A | 4/1965 | Bartels |
| 3,343,532 A | 9/1967 | Zumaglini |
| 3,364,926 A | 1/1968 | Alderson |
| 3,765,412 A | 10/1973 | Ommaya et al. |
| 3,776,224 A | 12/1973 | McFarland |
| 3,889,664 A | 6/1975 | Heuser et al. |
| 4,539,979 A | 9/1985 | Bremer |
| 4,620,530 A | 11/1986 | Lanier et al. |
| 4,886,052 A | 12/1989 | Calabrese |
| 4,913,135 A | 4/1990 | Mattingly |
| 5,005,563 A | 4/1991 | Veale |
| 5,046,490 A | 9/1991 | Young et al. |
| 5,109,835 A | 5/1992 | McDonald et al. |
| 5,195,947 A | 3/1993 | Bode |
| 5,330,516 A | 7/1994 | Nathan |
| 5,367,825 A | 11/1994 | Doring |
| 5,403,266 A | 4/1995 | Bragg et al. |
| 5,441,479 A | 8/1995 | Chitwood |
| 5,454,781 A | 10/1995 | Chitwood |
| 5,507,718 A | 4/1996 | Kabat |
| 5,569,176 A | 10/1996 | Graham |
| 5,651,754 A | 7/1997 | Chen |
| 5,651,764 A | 7/1997 | Chiu |
| 5,697,894 A * | 12/1997 | Gullichsen ............... A61F 5/04 602/17 |
| 5,728,054 A | 3/1998 | Martin |
| 5,752,927 A | 5/1998 | Rogachevsky |
| 5,823,982 A | 10/1998 | Park |
| 5,916,185 A | 6/1999 | Chitwood |
| 5,950,628 A | 9/1999 | Dunfee |
| 6,036,664 A | 3/2000 | Martin, Sr. et al. |
| 6,045,522 A | 4/2000 | Grober |
| 6,050,965 A | 4/2000 | Pillai |
| 6,059,548 A | 5/2000 | Campbell et al. |
| 6,368,295 B1 | 4/2002 | Lerman |
| 6,447,468 B1 | 9/2002 | Hankins et al. |
| 6,599,257 B2 * | 7/2003 | Al-Obaidi ............ A61H 1/0296 482/10 |
| 6,875,189 B1 | 4/2005 | Nelson |
| 6,899,690 B2 | 5/2005 | Saunders et al. |
| 6,984,217 B2 | 1/2006 | Becerra et al. |
| 7,048,705 B2 | 5/2006 | Pillai et al. |
| 7,128,724 B2 * | 10/2006 | Marsh ..................... A61F 5/055 602/17 |
| 7,166,063 B2 | 1/2007 | Rahman et al. |
| 7,608,052 B1 * | 10/2009 | Baker ..................... A61F 5/055 128/DIG. 23 |
| 8,758,285 B2 * | 6/2014 | Dallison ................. A61F 5/01 602/61 |
| 2006/0136998 A1 * | 6/2006 | Oowaki ................. G06F 21/31 726/5 |

\* cited by examiner

TRACTION APPARATUS AND METHODS

PRIORITY AND RELATED APPLICATIONS

This application is a divisional of and claims priority to co-owned, U.S. patent application Ser. No. 12/069,134 filed on Feb. 6, 2008 of the same title, and issuing as U.S. Pat. No. 8,905,958 on Dec. 9, 2014, which is incorporated herein by reference in its entirety. This application is related to co-owned U.S. Pat. No. 7,128,724 issued Oct. 31, 2006 entitled "Cervical Spine Brace and Traction Device", which is incorporated herein by reference in its entirety.

COPYRIGHT

A portion of the disclosure of this patent document contains material that is subject to copyright protection. The copyright owner has no objection to the facsimile reproduction by anyone of the patent document or the patent disclosure, as it appears in the Patent and Trademark Office patent files or records, but otherwise reserves all copyright rights whatsoever.

BACKGROUND OF THE INVENTION

1. Field of the Invention

The present invention relates generally to apparatus and methods for utilizing and monitoring traction-based therapy, and specifically in one exemplary aspect to a mobile cervical spine brace and traction device which is able to provide electronic data regarding use to a patient and/or operator.

2. Description of Related Technology

By age 55, about 95% of the population will experience some degenerative condition of the cervical spine that may cause neck pain and/or upper extremity pain and as much as one-third of that group may experience weakness. These non-tumorous and non-infectious conditions may include degenerative intervertebral discs, disc herniations, internal disc disruption, vertebral osteophytes or spur formation and spondylolisthesis, and they may potentially result in loss of disc space, height, encroachment on spinal nerve roots where they exit the spinal cord (radiculopathy), regional spinal cord compression (myelopathy) or vertebral joint instability. Moreover, yearly work-injury-related neck and/or back pain may frequently affect as much as 15 to 20% of the workforce; for example, the 1990 annual cost of neck and lower back care in the United States reached a staggering $85 billion.

Management of cervical pain, radiculopathy and myelopathy is either surgical or conservative; these surgical or conservative approaches may include anti-inflammatory medications, physical therapy, immobilization and traction. Surgical patients are always at risk for surgical complications including resultant quadriplegia and even death. Many recent publications by surgical and conservative therapists have, both retrospectively and prospectively, compared short and long term outcomes between the two treatment groups, and the consensus appears to be that, in the majority of patients, the outcomes are not truly distinguishable at one year. Further, an intervention that would hasten the conservative recovery process, such as by facilitating independent patient participation in hislher own care, would result in significant healthcare cost savings.

Cervical traction is a technique where the weight of the head is removed from the cervical spinal axis and the cervical column is stretched in order to relieve stress within the neck. This method can temporarily remove much of the pain experienced by people with cervical disorders. Traction devices are well known in the medical field to facilitate the accomplishment of the following: (i) regaining normal length and alignment of involved bone, (ii) reducing and immobilizing fractured bone, (iii) lessening or eliminating muscle spasms, (iv) relieving pressure on nerves, especially spinal nerves, and (v) preventing or reducing skeletal deformities or muscle contractures. However, most of the currently available traction devices are very cumbersome and difficult to use. Also, many must be used with direct interaction with a physician or other health care provider and, therefore, deny the patient mobility when in traction. Because these problems often affect the everyday lives of these patients, a portable traction device that can be used while the person goes about his daily tasks can prove to be a far better solution.

Previous mechanical efforts to support the cervical spine or apply traction thereto have generally fallen into certain distinct design categories.

One such category includes cervical collars that incorporate single or multiple, stacked pneumatic/air bladders. These devices are shown at inter alia, U.S. Pat. Nos. 6,050,965; 7,048,705; 5,752,927; 3,765,412; 6,059,548; 6,899,690; 6,447,468; 5,916,185; 5,454,781; 5,441,479; 5,569,176; and 3,343,532. Cervical collars incorporating multiple, stacked, fluid-filled bladders are shown at, inter alia, U.S. Pat. Nos. 5,823,982; and 5,403,266. The solid nature of the abovementioned collars makes such apparatus difficult for a patient to use while engaging in other activities. Furthermore, the use of fluid or air filled bladders typically renders the prior art devices non-durable thereby impeding a user from participating in various common activities during traction therapy.

A full, but open, cervical collar, attached to a heavy chestlback apron/harness by adjustable spring-loaded rods is shown in U.S. Pat. No. 6,045,522; whereas U.S. Pat. No. 3,776,224 shows a similar spring-tensioned device. Such devices again disrupt a patient's ability to engage in normal activities while wearing the device as well as require physician or other professional operation.

U.S. Pat. No. 2,102,069 shows spaced pads carried by independent side braces that are angularly adjustable and are also longitudinal adjustable via sliding members and clamping screws. Threaded rod adjusters are shown in U.S. Pat. Nos. 2,736,314; 2,820,455; and 3,177,869. U.S. Pat. No. 5,046,490 places a peg in a hole on a sliding bar to fix the length and employs a hinge mechanism to control abduction in one embodiment and, in another, uses nuts on a threaded rod to cause a collar to slide up and down.

A rack and pinion system is shown in U.S. Pat. No. 2,791,999. A halo to skull fixation device is attached to shoulder harness by calibrated threaded rods in U.S. Pat. No. 5,195,947 and in U.S. Pat. No. 5,697,894.

A full collar with a tracheal core aperture designed for static support and emergency immobilization is shown in U.S. Pat. No. 4,886,052 and a full collar with a ratchet and pawl mechanism for improved fit, emergency immobilization is shown in U.S. Pat. No. 6,036,664.

U.S. Pat. No. 5,651,754 illustrates a device for reforming the spine which utilizes a belt that is tightened about the waist and a motor-driven vertical rod that spaces a brace that engages the arm pits or the chin.

U.S. Pat. No. 6,875,189 to Nelson shows a cervical traction device which utilizes, inter alia, a hinge to attach the occipital support to the main body. U.S. Pat. No. 6,599,257 illustrates a cervical therapy device which allows rotation about two perpendicular axes and linear movement along one of these axes.

Despite the breadth of the foregoing variations, there is a need for improved apparatus and methodology for traction-based therapy. Such improved apparatus and methodology would ideally provide a patient with a user-friendly, simple, lightweight, easily installed and easily adjusted device which allows the application of appropriate, effective and efficient cervical traction by the patient in any setting; e.g., while the patient is an upright, mobile position, or while still permitting continuous passive motion by the patient (such as e.g., allowing them to rotate their head to either side).

Such apparatus and methods would furthermore advantageously implement data collection and transmission elements, as well as be adapted to provide a physician, physical therapist, chiropractor or other healthcare provider (or even the patient themselves) with the ability to program in the apparatus a regimen for the patient to follow, as well as incorporate monitoring functionality for the healthcare provider.

SUMMARY OF THE INVENTION

The present invention satisfies the foregoing needs by providing, inter alia, a device which is capable of providing both cervical spine support as a brace and adjustable symmetric and asymmetric cervical spine traction in an entirely portable fashion. It may be electronically or manually controlled, and is adapted to record information regarding a patient's use of the apparatus for later analysis.

In a first aspect of the invention, traction apparatus is disclosed. In one embodiment, the apparatus comprises: a collar member, and a head member, the head member being mated to the collar member such that the head member can rotate relative to the collar member around a first axis, yet not move substantially in a direction longitudinal along the axis. The rotation allows the head of a wearer of the apparatus to rotate, yet substantially maintains a prescribed degree of traction on the spine thereof.

In a second embodiment, the traction apparatus comprises: a collar member adapted to mate with the collar region of a human being; a head member, the head member being mated to the collar member in a substantially rotatable relationship; at least one sensor; and data storage apparatus, the data storage apparatus adapted to store data generated by the at least one sensor for subsequent use.

In one variant, the at least one sensor comprises a force or strain sensor.

In another variant, the at least one sensor comprises an accelerometer.

In yet another variant, the at least one sensor comprises a rotation or position sensor adapted to sense the relative position of the collar member and the head member.

In a further variant, the apparatus further comprises a network interface adapted to transmit the data from the apparatus to a remote location over a network. The network comprises e.g., a wireless local area network (LAN).

In still another variant, the apparatus further comprises a processor and computer program adapted to run thereon, the computer program being configured to monitor the at least one sensor and generate an alarm condition if one or more prescribed criteria are violated while the user is wearing the apparatus.

In yet another variant, the apparatus further comprises a force adjustment mechanism; and a processor and computer program adapted to run thereon, the computer program being configured to cause adjustment of the force adjustment mechanism. Adjustment of the mechanism is performed in one case in response to a command issued from a remotely located computerized device.

In a second aspect of the invention, a cervical spine brace and traction apparatus is disclosed. In one embodiment, the apparatus comprises (i) a collar member being forwardly opening and being further comprised of a pair of lateral wall sections, the wall sections each having a laterally extending bracket and an inter-engaging means adapted to maintain alignment of the walls with respect to one another, a region adapted to rest on the shoulders of a wearer, and a landing inlet adapted to receive a protruding tab of a head brace member; (ii) a head brace member being forwardly opening and being further comprised of a protruding tab adapted to be received within the landing inlet of the collar member, and a head support region contoured to fit against the occipital region of the head of the wearer; (iii) a microprocessor adapted to store data, run at least one computer application, and transmit the stored data; and (iv) a traction adjustment member comprising at least one sensor adapted to transmit sensed data to a microprocessor; at least one upwardly extending, rotatable rod mechanism supported by each of the brackets, the rod mechanism having a pair of coaxial right-handed and left-handed lead screw surfaces. According to this embodiment, traction may be applied to the cervical spine of the wearer by causing the head brace to be 'smoothly raised above the collar member or in a desired position.

In one variant, the head brace member extends forwardly from the occipital support region to a pair of regions which support each mandible of the wearer at its normal angle. In another variant, the at least one sensor comprises at least one accelerometer. In yet another embodiment, the at least one sensor comprises at least one force gauge. In another embodiment, the at least one sensor comprises, at least one timer function.

In yet another variant, each of the brackets includes a mating threaded portion interconnected with one of the lead screw surfaces. In one variant, the traction adjustment member further comprises a unit in which a miter gear is rotatably mounted to engage a cooperative miter gear which is affixed as part of the rod mechanism. In another variant, the traction adjustment member further comprises a finger-manipulable adjustor connected to a shaft for rotating the miter gear and wherein the unit is supported from the rod mechanism. In yet another variant, each rod mechanism includes stop means associated with at least one lead screw surface for limiting the extent to which the spacing between the collar member and the head brace can be extended. In another variant, the microprocessor is further adapted to control the function of an electronic control mechanism, the electronic control mechanism is adopted to control an electronic motor, and the electronic motor is adapted to electronically turn the miter gear.

In still another variant, the at least one computer application comprises a therapy program, the therapy program causing the microprocessor to receive and implement program criteria via the electronic control mechanism. In another variant, the program criteria comprises at least one of the maximum and/or minimum duration of use, the maximum and/or minimum force of distraction, the maximum and/or minimum extent of distraction, and the maximum and/or minimum degree of rotation. In another variant, the apparatus further comprises an alarm or signal, the alarm or signal adapted to be triggered by a breach of any one of the program criteria. In one option, the alarm or signal comprises a multi-colored LED light; in another option, the alarm or signal comprises an audible signal and in a final option, the alarm or signal comprises a reminder, the reminder comprising an electronic message.

In yet a further variant, the program criteria are stored on the microprocessor.

In yet another variant, the apparatus further comprises a user interface wherein the program criteria are entered by a user.

In another variant, the stored data stored comprises data regarding at least one of: the degree of rotation of the head brace member, the force of distraction, the extent of distraction, and the duration of use. In one variant, the stored data is transmitted to a remote device. The remote device may comprise a device registered with a database associated with the apparatus; the transmission may be wireless; and the receiving device may comprise a personal computer.

In still another variant, the inter-engaging means comprises at least one vertical slot on one of the lateral wall sections, and at least one elongated lug on the other of the lateral wall sections, the elongated lug slidably received in the vertical slot.

In a further variant, at least one of the head brace member protruding tab and the collar member landing inlet is coated in a friction reducing agent. In one variant, the friction reducing agent comprises Teflon.

In yet another variant, the collar member further comprises an adjustable Velcro strap adapted to secure the collar member on the wearer's shoulders. Another variant has the head brace member further comprised of an adjustable Velcro strap adapted to secure the head brace member on the wearer's head.

In another variant, the head support region contoured to fit against the occipital region of the head of the wearer further comprises conforming pads. Another variant has the lateral region adapted to rest on the shoulders of the wearer further comprised of conforming pads.

In a third aspect of the invention, a cervical spine brace and traction apparatus is disclosed. In one embodiment, the apparatus comprises (i) a collar member being forwardly opening and comprised of a pair of lateral wall sections, the wall sections each having a laterally extending bracket and an inter-engaging means adapted to maintain alignment of the walls with respect to one another, a region adapted to rest on the shoulders of a wearer, and a landing inlet adapted to receive a protruding tab of a head brace member; (ii) a head brace member being forwardly opening and comprised of a protruding tab adapted to be received within the landing inlet of the collar member, and a head support region contoured to fit against the occipital region of the head of the wearer; (iii) a microprocessor adapted to store data, run at least one computer application, and transmit the stored data; and (iv) an electronically controlled traction adjustment member comprising at least one sensor adapted to transmit sensed data to the microprocessor; at least one upwardly extending, rotatable rod mechanism supported by each of the brackets, the rod mechanism having a pair of coaxial right-handed and left-handed lead screw surfaces, a motor device adapted to control rotation of the rotatable rod mechanism, and an electronic control mechanism in electronic communication with the microprocessor and being adapted to control the function of the motor device; wherein traction may be applied to the cervical spine of the wearer by causing the head brace to be smoothly raised above the collar member or in a desired position.

In a fourth aspect Of the invention, a method of using a cervical spine brace and traction apparatus is disclosed. In one embodiment, the method comprises disposing the apparatus on a subject; adjusting distraction of the apparatus; recording adjustment data; and transmitting the adjustment data.

In one variant, the act of adjusting distraction of the apparatus comprises manual adjustment of the apparatus. In one variation, the manual adjustment is accomplished by rotation of a starwheel. In yet another variant, the manual adjustment further comprises the placement of stopping mechanisms on an adjustment mechanism so as to create a maximum and/or minimum permissible distraction.

In another variant, the act of adjusting distraction of the apparatus comprises electronic adjustment of the apparatus. In yet another variant, the electronic adjustment is accomplished via an electronic control mechanism adapted to control a motorized distraction adjustment mechanism.

In yet another variant, the method further comprises running a computer application adapted to cause a microprocessor on the apparatus to receive and implement program criteria.

In yet another variant, the program criteria is entered by a user, the program criteria comprising at least one of: the maximum and/or minimum duration of use, the maximum and/or minimum force of distraction, the maximum and/or minimum extent of distraction, and the maximum and/or minimum degree of rotation. In another variation, the method further comprises triggering an alarm or signal if the entered criteria are not met, the alarm or signal comprising at least one of illumination of a multi-colored LED light, triggering of an audible signal, or sending an electronic message.

In still another variant, the program criteria is selected among stored program criteria on the microprocessor; the program criteria comprising at least one of the maximum and/or minimum duration of use, the maximum and/or minimum force of distraction, the maximum and/or minimum extent of distraction, and the maximum and/or minimum degree of rotation.

In another variation, the method further comprises triggering an alarm or signal if the selected criteria are not met, the alarm or signal comprising at least one of illumination of a multi-colored LED light, triggering of an audible signal, or sending an electronic message.

In another variant, the recorded adjustment data comprises at least one of duration of use, degree of rotation, force of distraction, or extent of distraction. In one variant, the adjustment data is recorded to an internal storage device. In another variant, the adjustment data is transmitted to a remote device. In yet another variant, the remote device comprises a device registered with a database associated with the apparatus. The transmission may also be wireless in one variant. And, in another variant, the registered remote device comprises a personal computer, the personal computer adapted to receive the adjustment data.

In a fifth aspect of the invention, a system for the use and analysis of a traction-based therapy is disclosed. In one embodiment, the system comprises a cervical spine brace and traction apparatus adapted to perform traction-based therapy; a recording element, the recording element adapted to record adjustment data from the traction-based therapy; a transmitting element, the transmitting element being adapted to transmit the adjustment data to a receiving device; a receiving device, the device being adapted to receive the adjustment data; and an analysis mechanism, the analysis mechanism adapted to run on the receiving device and to analyze the received adjustment data.

In one variant, the cervical spine brace and traction apparatus adapted to perform traction-based therapy further comprises a manually adjustable traction mechanism. In one variant, the cervical spine brace and traction apparatus adapted to perform traction-based therapy further comprises an electronically adjustable traction mechanism adapted to perform at least one programmed traction therapy program, the program stored on a microprocessor on the apparatus.

In yet another variant, the cervical spine brace and traction apparatus adapted to perform traction-based therapy further comprises an electronically adjustable traction mechanism adapted to receive and implement a traction therapy program, the traction therapy program comprising user-entered program criteria, the criteria entered into a microprocessor on the apparatus adapted to control the traction of the apparatus.

In yet another variant, the program criteria comprise at least one of the maximum and/or minimum duration of use, the maximum and/or minimum force of distraction, the maximum and/or minimum extent of distraction, the maximum and/or minimum degree of rotation.

In yet another variant, the adjustment data comprises at least one of duration of use, degree of rotation, force of distraction, or extent of distraction.

In yet another variant, the recording element comprises an external storage device in electronic communication with the apparatus.

In yet another variant, the recording element comprises an internal storage device.

In another embodiment, the transmitting element comprises a wired connection to the receiving device. Alternatively, in another embodiment, the transmitting element comprises a wireless connection to the receiving device. In one variant, the receiving device is authenticated by registration with a registration database. In yet another variant, the receiving device comprises a personal computer, and in yet another variant, the analysis mechanism comprises a computer application running on the personal computer.

In a sixth aspect of the invention, a system for the utilization of traction-based therapy is given. In one embodiment, the system comprises a means for applying traction to the cervical spine of a subject; a means for recording adjustment data from the application of traction; a means for transmitting the adjustment data to a receiving device; a means for receiving the adjustment data; and a means for analyzing the adjustment data.

In one variant, the means for applying traction to the cervical spine of a subject is accomplished via a manually adjustable traction mechanism.

In yet another variant, the means for applying traction to the cervical spine of a subject is accomplished via an electronically adjustable traction mechanism adapted to perform at least one programmed traction therapy program, the program stored on a microprocessor.

In yet another variant, the means for applying traction to the cervical spine of a subject is accomplished via an electronically adjustable traction mechanism adapted to receive and implement user-entered program criteria, the criteria entered into a microprocessor adapted to control the adjustment of traction. In one variant, the user-entered program criteria comprise at least one of the maximum and/or minimum duration of use, the maximum and/or minimum force of distraction, the maximum and/or minimum extent of distraction, and the maximum and/or minimum degree of rotation.

In yet another variant, the adjustment data comprises at least one of duration of use, degree of rotation, force of distraction, or extent of distraction.

In still another variant, the means for recording comprises an external storage device in electronic communication with the apparatus. In another variant, the means for recording comprises an internal storage device.

In another variant, the means for transmitting comprises a wired connection to the means for receiving. In on variant, the means for transmitting comprises a wireless connection to the receiving device.

In a further variant, the means for receiving is authenticated by registration with a registration database. In one variation, the means for receiving comprises a personal computer. In yet another variant, the means for analyzing comprises a computer application running on the means for receiving.

In a seventh aspect of the invention, a computer readable apparatus is disclosed. In one embodiment, the apparatus comprises a storage medium adapted to store a computer program adapted to run on a personal device and to receive and display adjustment data from a cervical spine brace and traction device; compare the adjustment data to pre-programmed standards; track a user's progress with regard to pre-programmed standards; make recommendations regarding enhancement of a user's traction-based therapy progress; and transmit periodic updates to a set of pre-determined locations.

In one variant, the personal device comprises anyone of a personal computer, a PDA device, or a web-enabled digital telephone.

In yet another variant, the adjustment data comprises data regarding at least one of: the degree of rotation of the cervical spine brace and traction device, the force of distraction of the cervical spine brace and traction device, the extent of distraction of the cervical brace and traction device, or the duration of use of the cervical spine brace and traction device.

In yet another variant, the pre-programmed standards comprise standards entered by a healthcare provider prior to use.

In yet another variant, the pre-determined locations comprise IP addresses of previously registered devices.

In another embodiment, the apparatus comprises a storage medium adapted to store a computer program adapted to run on a microprocessor in communication with a cervical spine brace and traction device and to enable a user to enter identifying information; enable a user to enter program specifications to create a therapy program; alert a user when certain program specifications are breached; and transmit periodic updates to a set of pre-determined locations.

In one variant, the microprocessor comprises a microprocessor located within a cervical spine brace and traction device.

In yet another variant, the program specifications comprise at least one of the maximum and/or minimum duration of use, the maximum and/or minimum force of distraction, the maximum and/or minimum extent of distraction, the maximum and/or minimum degree of rotation.

In yet another variant, the pre-determined cations comprise IP addresses of previously registered devices.

In a ninth aspect of the invention, traction apparatus is disclosed. In one embodiment, the apparatus comprises: a collar apparatus adapted to mate with the collar region of a subject; a head support apparatus, the head support apparatus being mated to the collar apparatus by association through at least one substantially adjustable support member, the at least one support member comprising at least one mechanism for moving the head support apparatus relative to the collar apparatus so as to increase or decrease the traction applied to a user.

In one variant, the at least one substantially adjustable support member comprises a single substantially vertical beam.

In another variant, the apparatus further comprises: at least one sensor; and a data storage apparatus, the data storage apparatus adapted to store data generated by the at least one sensor.

In yet another variant, the head support apparatus comprises first and second elements, the first element adapted to rotate relative to the second element around a first axis, yet not move substantially in a direction longitudinal along the axis. The first axis is substantially parallel and coincident with a spinal column of the user for example. The head support apparatus can also be made to rotate relative to the collar apparatus around a second axis.

In still another variant, the rotation allows the head of the user to rotate, yet substantially maintains a prescribed degree of traction on the spine thereof.

In a further variant, the at least one sensor comprises a force or strain sensor. Alternatively, the sensor comprises an accelerometer. As yet another alternative, the at least one sensor comprises a rotation or position sensor adapted to sense the relative position of the first and second elements of the head support apparatus.

In another variant, the apparatus further comprise a network interface adapted to transmit the data from the apparatus to a remote location over a network, such as e.g., a WLAN interface.

The apparatus further comprises a processor and computer program adapted to run thereon, the computer program being configured to monitor the at least one sensor and generate an alarm condition if one or more prescribed criteria are violated while the user is wearing the apparatus.

In still a further variant, the apparatus further comprises: a force adjustment mechanism; and a processor and computer program adapted to run thereon, the computer program being configured to cause adjustment of the force adjustment mechanism. The adjustment of the mechanism is performed in response to a command issued from a remotely located computerized device.

These and other features of the invention will become apparent from the following description of the invention, taken in conjunction with the accompanying drawings.

DETAILED DESCRIPTION OF THE INVENTION

Figure 1:
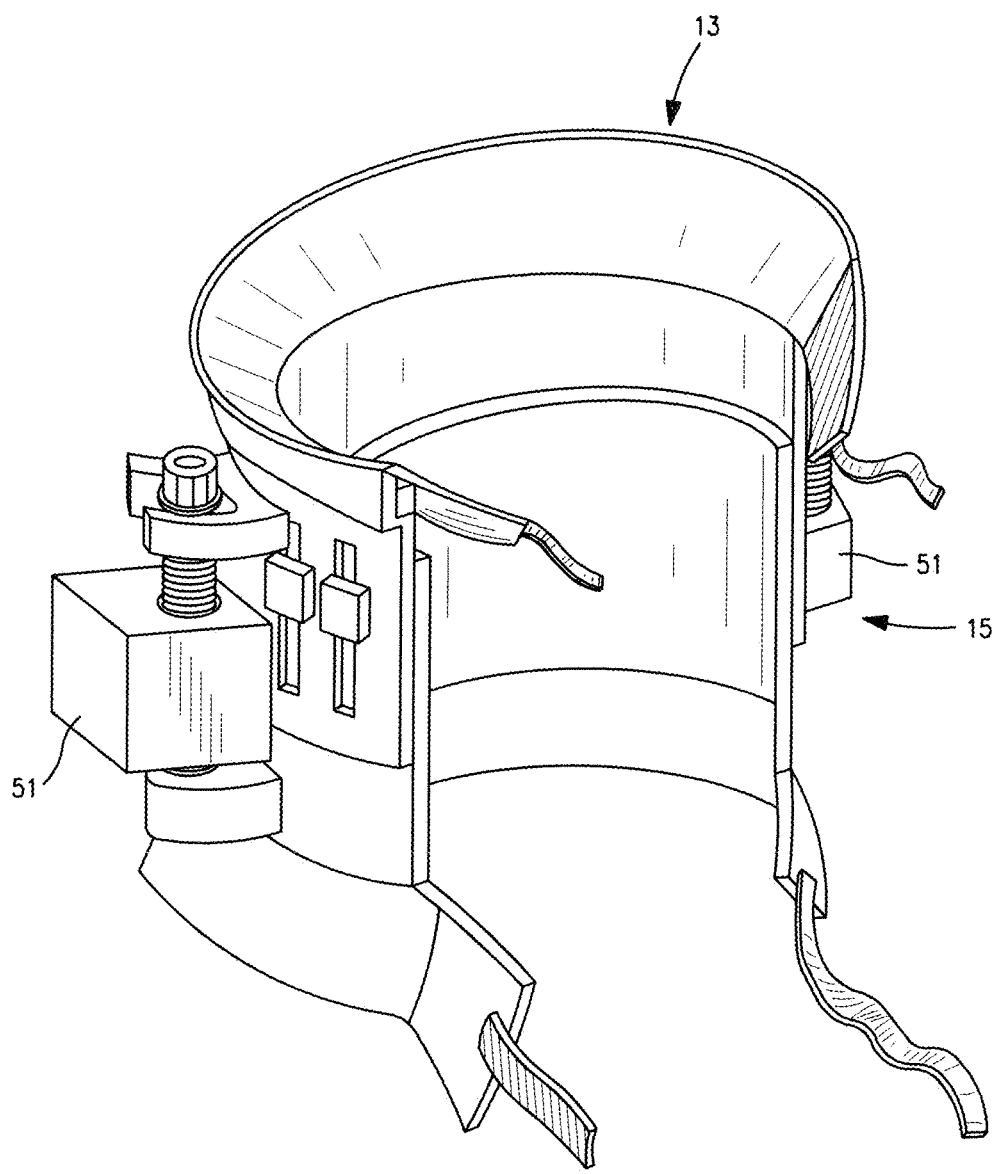
FIG. 1 is a perspective view of one exemplary embodiment of a traction device according to the present invention.

Reference is now made to the drawings wherein like numerals refer to like parts throughout.

As used herein, the term "application" refers generally to a unit of executable software that implements a certain functionality or theme. The themes of applications vary broadly across any number of disciplines and functions (such as content management, e-commerce transactions, brokerage transactions, home entertainment, calculator etc.), and one application may have more than one theme. The unit of executable software generally runs in a predetermined environment; for example, the unit could comprise a downloadable Java Xlet™ that runs within the JavaTV™ environment.

As used herein, the terms "cervical" and "cervical vertebrae" pertain to those vertebrae immediately caudual to (or behind) the skull in a human subject.

The term "component" in the context of software refers generally to a unit or portion. of executable software that is based on a related set of functionalities. For example, a component could be a single class in Java™ or C++. Similarly, the term "module" refers generally to a loosely coupled yet functionally related set of components.

As used herein, the term "computer program" is meant to include any sequence or human or machine cognizable steps which perform a function. Such program may be rendered in virtually any programming language or environment including, for example, CIC++, Fortran, COBOL, PASCAL, assembly language, markup languages (e.g., HTML, SGML, XML, VoXML), and the like, as well as object-oriented environments such as the Common Object Request Broker Architecture (CORBA), Java™ (including J2ME, Java Beans, etc.) and the like.

As used herein the terms "distraction" and "distracted" are intended to refer to without limitation the application. of forces to a subject's skeletal system, e.g. the vertebral column. The application of forces may include, but is not limited to, vertebral traction and vertebral decompression.

As used herein, the term "integrated circuit (IC)" refers to any type of device having any level of integration (including without limitation ULSI, VLSI, and LSI) and irrespective of process or base materials (including, without limitation Si, SiGe, CMOS and GaAs). ICs may include, for example, memory devices (e.g., DRAM, SRAM, DDRAM, EEPROM/Flash, 20 ROM), digital processors, SoC devices, FPGAs, ASICs, ADCs, DACs, transceivers, memory controllers, and other devices, as well as any combinations thereof.

As used herein, the term "memory" includes any type of integrated circuit or other storage device adapted for storing digital data including, without limitation, ROM. PROM, EEPROM, DRAM, SDRAM, DDR12 SDRAM, EDO/FPMS, RLDRAM, SRAM, "flash" memory (e.g., NANDI-NOR), and PSRAM.

As used herein, the terms "microprocessor" and "digital processor" are meant generally to include all types of digital processing devices including, without limitation, digital signal processors (DSPs), reduced instruction set computers (RISC), general-purpose (elSe) processors, microprocessors, gate arrays (e.g., FPGAs), PLDs, reconfigurable compute fabrics (ReFs), array processors, secure microprocessors, and application-specific integrated circuits (ASICs). Such digital processors may be contained on a single unitary IC die, or distributed across multiple components.

As used herein, the term "network interface" refers to any signal, data, or software interface with a component, network or process including, without limitation, those of the Firewire (e.g., FW400, FW800, etc.), USB (e.g., USB2), Ethernet (e.g., 10/100, 10/10011000 (Gigabit Ethernet), 1O-Gig-E, etc.), MoCA, Serial ATA (e.g., SATA, e-SATA, SATAII), Uitra-ATAIDMA, Coaxsys (e.g., TVnet™), radio frequency tuner (e.g., in-band or OOB, cable modem, etc.), WiFi (802.11a,b,g,n), WiMAX (802.16), PAN (802.15), or IrDA families.

As used herein, the term "pneumatic" refers generally to any apparatus moved or worked on by a pressurized gaseous medium (e.g. air, nitrogen, etc.), or otherwise comprising gas filled cavities.

As used herein, the tenn "traction" is meant to include any of the set of mechanisms for straightening broken bones or relieving pressure on the skeletal system through the application of a longitudinal force to the axis of the spinal column, such that parts of the 15 spinal column are pulled in opposite directions from one another in order to stabilize or change the position of damage aspects of the spine.

As used herein, the term "user interface" refers to, without limitation, any visual, graphical, tactile, audible, sensory, or other means of providing information to and/or receiving information from a user or other entity.

As used herein, the term "wireless" includes, but is not limited to, IS-95, CDMA2000, Wideband CDMA (WCDMA), BluetoothlM, IrDA interface, IEEE Std. 802.11 (a) or (g), Wireless Application Protocol (W AP), GPRS, GSM, TDMA (e.g., IS-54 or 136), UMTS, third-generation or "3G" systems such as 3GPP and 3GPP2, ultrawideband (UWB) systems such as TM-UWB or 802.15, WiMAX, satellite systems, or any other of myriad data communication systems and protocols well known to those of skill in the communications arts.

Overview

In one fundamental aspect, the present invention comprises a cervical spine brace and traction apparatus, and associated methods for use thereof. The apparatus incorporates a forwardly-open head and jaw brace with adjustable supports. Another salient aspect of the present invention is the mating of the brace and collar members of the apparatus. Specifically, in one embodiment these components are adapted to mate such that the brace is received within a landing inlet of the collar member. This inlet advantageously permits the brace to rotate to the subject's left and right (while remaining planar to the collar member), thereby permitting the subject wearing the apparatus to have a significant range of motion for his/her head.

Another aspect of the present invention relates to the creation of traction via cooperating lateral walls of the collar member. The lateral wall sections of the exemplary embodiment have mating arcuate surfaces that are juxtaposed and which include inter-engaging features that assure they remain precisely aligned with each other with respect to angle while the vertical spacing between them is being changed, i.e. traction. A rotatable rod mechanism having screw surfaces which pair with the threads of pairs of brackets extending laterally from each wall section creates the traction mechanism in one variant. A miter gear affixed to each rod in a central location mates with a cooperative miter gear affixed to a horizontal shaft that permits smooth and accurate patient adjustment. Adjustment may also be accomplished via an electronic motor or other electromechanical device controlled by e.g., a control mechanism and integrated circuit (e.g., microprocessor or microcontroller). The exemplary integrated circuit may be adapted to store information regarding a user's sessions, and optionally facilitate communication with patient and physician personal devices, thus sending these data from recorded sessions. The integrated circuit may also be adapted to implement therapy sessions based on heath care provider entered program specifications, or based on e.g., pre-programmed specifications.

DETAILED DESCRIPTION OF EXEMPLARY EMBODIMENTS

Referring now to FIGS. 1-7, exemplary embodiments and aspects of the invention are described in detail.

It is noted that while the invention is described herein primarily in terms of a method and apparatus for monitoring the use of a cervical brace such as during traction therapy, the invention may also be readily embodied or adapted to monitor other prescribed therapies at other locations on the human body including, but not limited to, thoracic and lumbar vertebrae, as well as monitoring the use of a cervical brace such as during traction therapy on other warm-blooded species. All such adaptations and alternate embodiments are readily implemented by those of ordinary skill in the relevant arts, and are considered to fall within the scope of the claims appended hereto.

It is further noted that, although the description below relates to placement of the traction apparatus on the neck and head of a subject thereby causing distraction of the cervical spine in order to relieve cervical radiculopathy; the traction apparatus described herein may likewise be employed in other medical processes including, inter alia, osteodistraction or distraction osteogenesis. Further, the apparatus described may be readily formed or shaped to accommodate other parts of the body, while still maintaining the advantageous features described herein, so as to distract the bones associated therewith for the purpose of either osteogenesis and/or relief from radiculopathetic conditions.

It is likewise appreciated that the traction apparatus of the present invention may also be advantageously adapted for use on subjects of various other species.

Apparatus for Traction-Based Therapy—

FIG. 1 depicts one embodiment of the traction device 11 of the present invention. As illustrated, the device 11 generally comprises an adjustable collar member 15 and a rotatable head brace 13 which fits within the collar member 15. The traction device 11 provides cervical spinal bracing and/or traction by exerting stretching force between the shoulders and a head brace 13 that is in contact with the occipital region of the head and extends forwardly (anteriorly) to support the angle and body of the mandibulae on each lateral side of the head.

Collar Member

Figure 2:
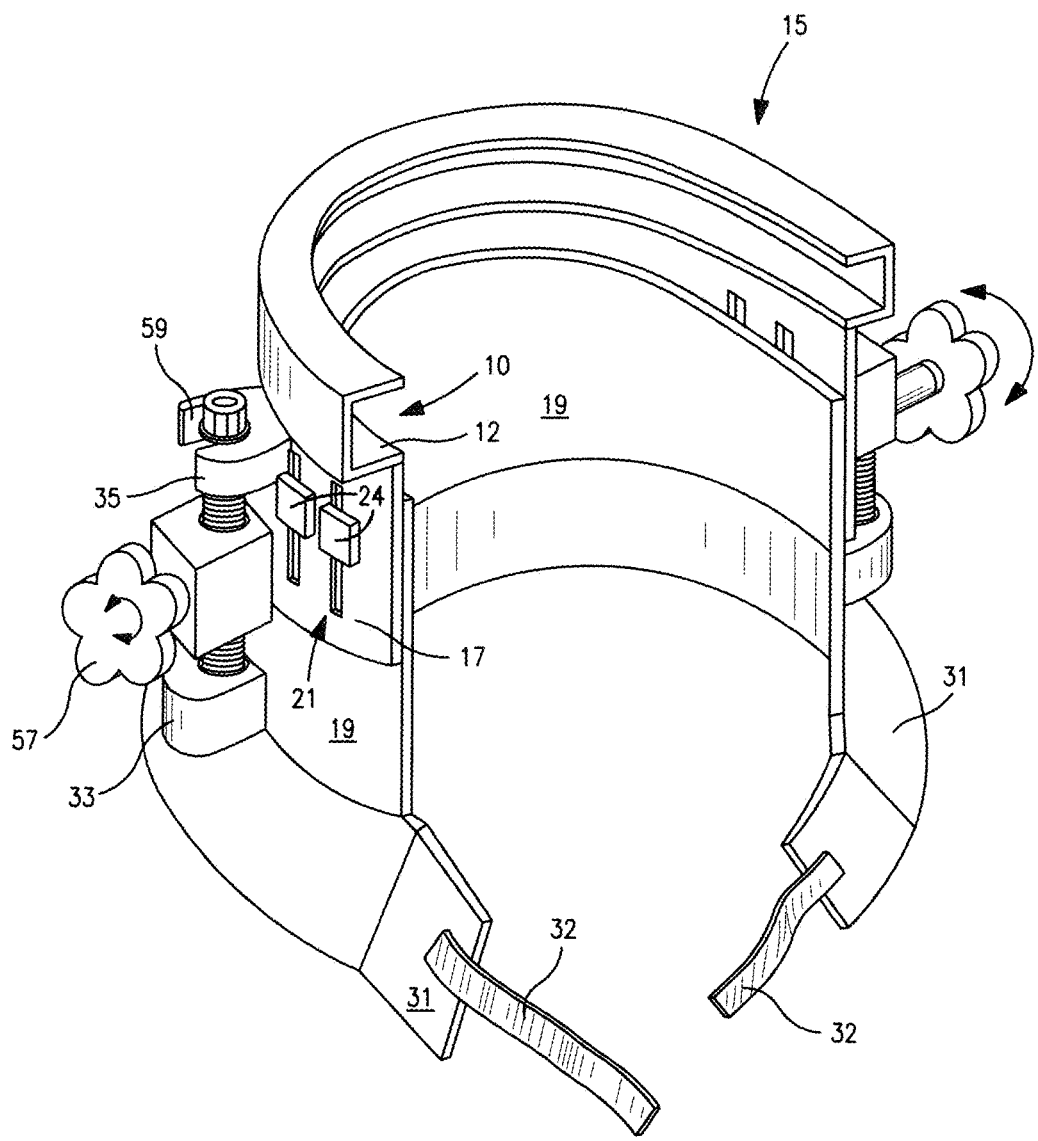
FIG. 2 is a perspective view of the collar member of the exemplary traction device of FIG. 1.

The collar member 15 of the traction device 11 is best illustrated in FIG. 2. The collar member 15 is advantageously forwardly open while being a continuous closed curve in the rear. The rear of the collar member 15 is also relatively narrow so as to permit a gap between the apparatus and rear portion of a subject's neck. This not only permits easy installation by the patient or wearer, but it facilitates ancillary treatment to allow concurrent therapy, as by the application of heat or cold to relieve pain or treatment with specific neuromuscular electrical stimulation, for example.

The collar member 15 is further comprised of two lateral wall sections 17, 19 which extend superiorly therefrom and are arranged, shaped, and proportioned to lie in a juxtaposed relationship with regard to one another. Inter-engaging means are utilized between the two juxtaposed wall sections 17, 19 to assure that the collar and the head brace are maintained in the precise alignment, i.e., angular orientation, one to the other, while the walls 17, 19 are being moved vertically either nearer together or further apart.

In the illustrated embodiment, the lateral wall sections 17, 19 have a shallow arcuate cross sectional shape with surfaces that have substantially the same radius of curvature so that the exterior surface of each lateral wall section 19 lies in contact with the interior surface of the depending lateral wall sections 17, as seen in FIG. 2. To facilitate this precise alignment while allowing such relative motion, the depending lateral wall sections 17 are preferably each provided with one or more parallel slots 21. In one embodiment, three slots 21 are utilized; two of which lie forward of the ear, with the third being positioned rear of the ear when a subject secures the apparatus to the neck. The slots 21 are preferably uniform in width throughout their length, and they receive parallel, rectangular guides 23 affixed to the exterior surface of each of the lateral wall sections 19 that extend superiorly from support region of the collar. These guides 23 are inter-engagingly, slidably received in the parallel slots 21, and the straight sidewalls of the rectangular guides 23 lie closely adjacent the elongated walls of the slots 21 and thus assure smooth relative motion between two walls 17, 19 in a precise direction both vertically and angularly. Moreover, the spacing of the singular slots 21 at a rearward location adds substantially to the overall stability of the spatial alignment. Once assembly is completed, small keepers 24 are affixed to the outer surfaces of the guides 23 by pins or the like to secure the inter-engagement. It will be appreciated that other means for securing the two walls 17, 19 to one another while maintaining smooth relative motion may be utilized consistent with the present invention including for example, tracks, sliders, threads, notches or other guides. Further, it will be appreciated that the number and placement of such inter-engaging means may be varied consistent with the present invention so as to increase stability and/or ease of motion between the walls 17, 19.

The collar member 15 further comprises a continuous curved undersurface, which is shaped and proportioned to lie comfortably on the shoulder girdle of the wearer at a location close to the base of the neck. It is constructed of material similar to that of the head brace 13 so as to preferably aesthetically resemble each other. Ends 31 of the open collar member 15 that terminate at the front opening are in the illustrated embodiment provided with inter-engaging Velcro straps 32. However, alternative fastening arrangements may be utilized consistent with the present invention so as to provide additional security and/or stability. In one embodiment (not shown), the undersurface of the collar member 15, i.e. the portion which will come into contact with a wearer's shoulders is provided with padding or cushioning material. The padding or cushioning may be comprised of a conformable substance such as air, or memory foam pads. In an alternate embodiment, the shoulder portion of the collar member 15 may be advantageously molded to the individual patient.

Head Brace

Figure 3:
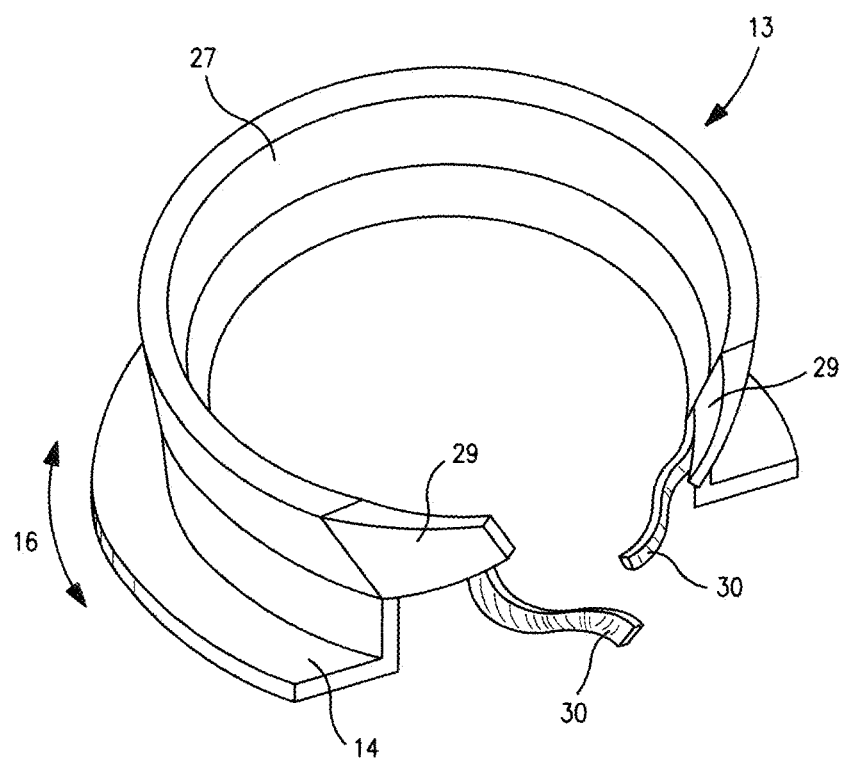
FIG. 3 is a perspective view of the head brace of the exemplary traction device of FIG. 1.
Figure 3A:
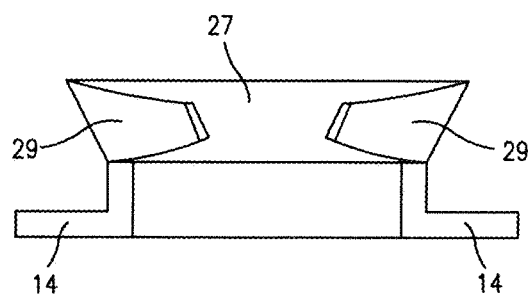
FIG. 3a is a front elevation view of the head brace of FIG. 3.

The head brace 13 of the traction device 11 is best illustrated in FIGS. 3 and 3a. The head brace 13 supports the occipital region of the head and is advantageously forwardly open while being in a continuous closed curve in the rear and permitting a space between the apparatus and subject's neck. As discussed above, this facilitates easy installation by the wearer as well as concurrent therapies.

The brace 13 preferably has a continuous curved or arcuate rear portion 27 that is contoured to comfortably abut the occipital region of the skull and a pair of oppositely disposed forward sections 29 that are contoured and angled to comfortably engage the undersurface of each mandible. It is preferably molded from a lightweight polymeric material; however, other suitable durable materials may be used. In the illustrated embodiment, a pair of inter-engaging Velcro hook and loop fastening straps 30 are affixed to the exterior surfaces of these front sections 29 so as to provide additional stability when the user is mobile; alternatively a single strap could be used that would attach to a strip affixed to the surface of the brace. The upper surface of the brace 13 is provided with padding or cushioning material (not shown), e.g. resilient polyurethane foam, or visco-elastic polyurethane foam (i.e., memory foam). Although the aforementioned components have been illustrated and described with regard to an exemplary embodiment, it should be understood that the scope of the invention is defined by the claims appended hereto and that changes and modifications as would be obvious to one having the ordinary skill in this art may be made without deviating therefrom, and that such changes may enhance the overall performance of the traction device 11. For 10 example, although the brace 13 and collar member 15 are discussed as being unitary in construction, each of them may be made in two or more pieces so as to be adjustable with each other (not shown).

Collar/Brace Interaction

Figure 4:
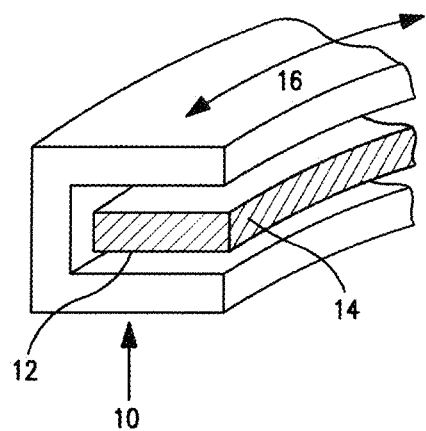
FIG. 4 is a partial sectional view of the of the exemplary traction device of FIG. 1, illustrating the interaction between the landing feature of the collar member and the protrusion of the head brace.

One salient aspect of the present invention is depicted in FIG. 4. As illustrated, the collar member 15 advantageously comprises a landing feature 10 (see also FIG. 2) adapted to receive the corresponding protrusion 14 of the head brace 13 (see also FIG. 3). Specifically, the landing feature 10 comprises a substantially horizontal inlet 12 having depth and height able to accommodate the length and height of the protrusion 14 respectively so as to facilitate continuous passive motion. FIG. 4 depicts the mating of the landing feature 10 of the collar member 15 with the protrusion 14 of the head brace 13.

As depicted, it is desirable that the dimensions of the inlet 12 be roughly similar to those of the protrusion 14 so as to accommodate the protrusion snugly and reduce tilting of the brace 13 when mated with the collar 15. It is also noted that the landing feature 10 extends throughout the periphery of the collar member 15 creating a landing inlet 12 that extends across the periphery of the collar member 15 and permitting mating of the protrusion 14 and inlet 12 around the periphery of the collar member 15. Further, the landing feature 10 is adapted so as to permit the mated brace 13 to rotate in the direction given by 16. In one embodiment, the protrusion 14 is advantageously coated with a friction reducing coating, such as Teflon®, etc. This coating permits unimpeded rotation of the head brace 13 about the vertical axis of the neck while maintaining the head brace 13 substantially parallel to the plane of the landing inlet 12. Thus, a patient will be permitted to rotate their head in a right or left direction while the subject's neck is simultaneously distracted.

Traction Mechanism

As discussed above, the present invention also beneficially provides traction therapy to cervical vertebrae. In order to accomplish this purpose, the apparatus comprises certain features adapted to enable the straightening or elongation of these vertebrae with respect to one another. The features discussed below (and depicted in the given figures) are merely exemplary in nature and are not intended represent the only embodiment of the present invention; rather, a plurality of mechanisms for accomplishing the traction function may be utilized consistent with the present invention.

Specifically, in one embodiment of the present invention (illustrated in FIG. 2) pairs of apertured brackets 33, 35 of generally similar construction which extend laterally from surfaces of the walls 17, 19 of the collar member are utilized. These brackets are provided to achieve the adjustment of the vertical spacing between the collar member 15 and the brace 13 when the two are mated, as discussed above. A pair of brackets 33, 35 comprises one lower bracket 33 which extends from the exterior surface of the upstanding wall 19, and one upper bracket 35 which extends from the exterior surfaces of the depending wall 17. It is appreciated that any number of bracket pairs may be utilized consistent with the present invention.

Figure 5:
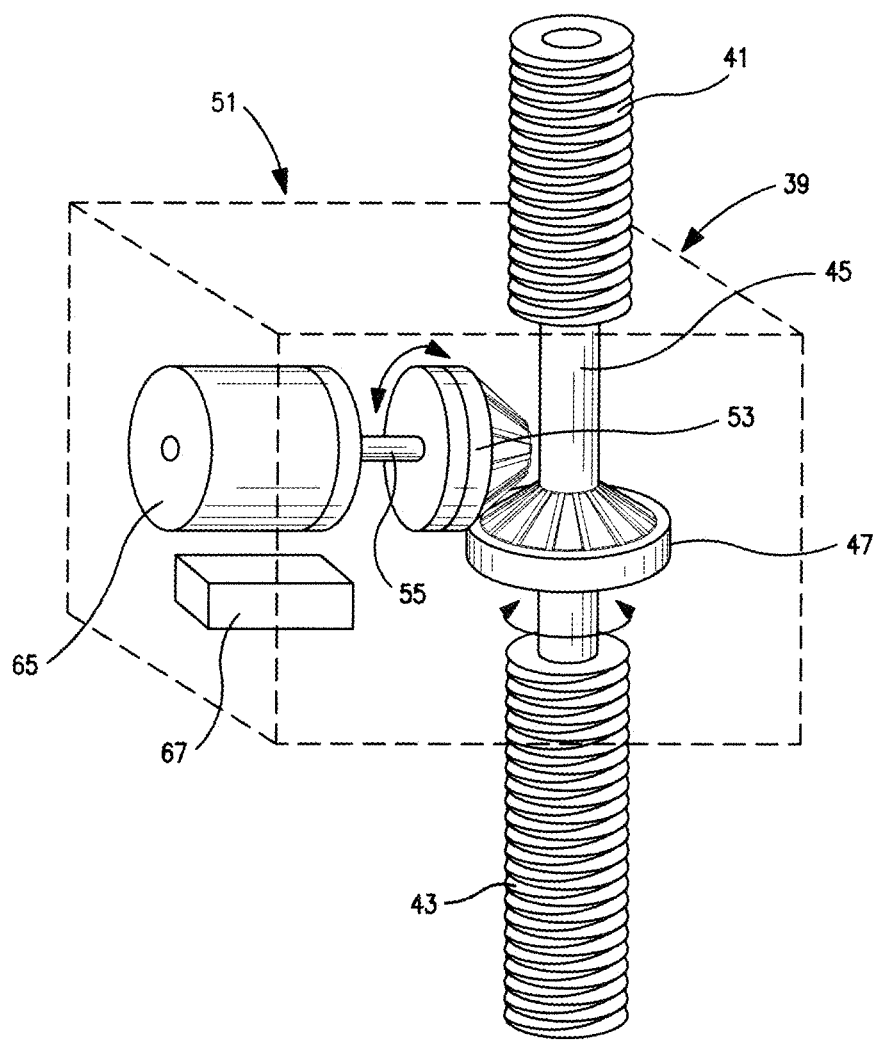
FIG. 5 is a cutaway perspective view one embodiment of the traction feature of the exemplary traction device of FIG. 1.

Referring now to FIG. 5, a rotatable rod mechanism 39 which is supported by and extends between the upper and lower brackets on each side of the device 11 is depicted. The rod mechanism 39 is designed to very precisely and smoothly adjust the vertical distance between the two walls of the collar 15 so as to either apply greater traction or reduce the traction force. As discussed above, the collar 15 is adapted to receive the head brace 13; accordingly, when the distance between the two walls is adjusted, the distance between that portion of the device 11 engaged with the head brace 13 and that portion resting on a patient's shoulders is adjusted. The rod mechanism 39 is designed so as to balance out any torque by creating driving engagements both at the location of the upper bracket 35 and at the location of lower bracket 33 on each side of the device, and in this way to positively avoid the likelihood of binding and to assure smooth movement.

In the illustrated embodiment, the rod 39 is one which has an upper lead screw surface 41 of one orientation, e.g., a right-handed thread, and a lower lead screw surface 43 of the opposite orientation, e.g., a left-handed thread. These screw threads are preferably cut into the surface of a rod of a suitable diameter so that the rod is an integral piece; however, the rod could be built as a composite member so long as the resultant structure has coaxial lead screw surfaces. A central section 45 of the rod 39, preferably located exactly halfway from each end, is of a reduced diameter, and it may be machined to have a miter gear surface 47, or alternatively such a gear may be affixed to the reduced diameter rod section. The upper and lower threaded sections 41, 43, which are preferably located at opposite ends of the rod 39, are received in the apertures of the brackets 35, 33. These apertures may be machined so as to have mating threads which inter-engage with the lead screw surfaces 41, 43 on the upper and lower sections of the rods, or the brackets 33, 35 may, in another embodiment (not shown), be molded so as to have hexagonal recesses in their facing surfaces into which metal nuts having mating threads are press fit and/or adhesively secured. In an alternative embodiment, the brackets 33, 35 might be bifurcated to provide horizontal slots into such nuts could be inserted and secured in alignment.

Accordingly, when the rod 39 is caused to be rotated clockwise as viewed from above, both rod threaded sections 41, 43 may enter more deeply into the brackets 35, 33 and thus cause the two walls 17, 19 of the collar member 15 to smoothly move toward each other, slightly reducing the amount of traction. Likewise, when the rod 39 is caused to be rotated counter-clockwise, both rob threaded sections 41, 43 disengage from the brackets 35, 33 and cause the two walls 17, 19 to smoothly move away from each other, thereby increasing the amount of traction.

To drive the rod mechanisms 39, a small gear box 51 is supported on each rod at the location of the central section 45 of reduced diameter. The gear box 51 has apertures in its upper and lower ends so that it is journalled on the rod itself, and it is preferably a rectangular parallelepiped for convenience of construction. It contains a miter gear 53 mounted on a horizontal shaft 55 that extends through the gear box 51 wall which the miter gear 53 meshes smoothly with the miter gear 47 affixed to the rod; thus, its rotation drives the rod 39 in either clockwise or counterclockwise rotation. The horizontal shaft 55 is journalled in the gear box wall, preferably by a suitable bearing (not shown), and it carries a knob in the preferable form of a starwheel 57 affixed to its outer end which the patient will use to turn the miter gears 53, 57, rotate the rod 39 and thus move the walls 17, 19 of the collar member 15 smoothly toward each other or away from each other.

The illustrated embodiment of FIG. 2 incorporates a starwheel 57 adjustment mechanism. It is appreciated, however, that the starwheel 57 is exemplary in nature and that a plurality of shapes or forms of adjustment mechanisms may be utilized consistent with the present invention, including, for example, a scissor mechanism, step-up mechanism, buckles, etc. Further, the adjustment mechanism (including a starwheel 57) may be located in a plurality of positions relative a user and any number of such mechanism may be utilized consistent with the present invention. The precise change that is possible in this manner provides a potential for objective calibration, i.e., the number of screw rotations needed to achieve one millimeter of distraction of intervertebral space. This use of the two lead screw surfaces of opposite threading and the miter gear arrangement allows for very gradual and precise changes in the spacing between the brace and the collar member, and thus allows "fine tuning" of the amount of traction being applied.

Because a physical therapist may wish to limit the amount of traction that any individual patient can apply at anyone time during rehabilitation, FIG. 2 further depicts a locking clamp, a locking washer or nut or other such stop 59, which is preferably provided near the end of one of the lead screw surfaces of each rod 39. Illustrated is such a stop clamp 59 which is manufactured to have an interior surface that inter-engages with the threads 41 at the upper end of the rod.

It might be molded from a rigid plastic or preferably made of metal; it is designed to snap around the threaded rod and remain tightly in one place. A short tang extends from a central location to allow its easy placement or removal. Thus, it allows the physical therapist to set a maximum distance to which the brace and the collar member can be spaced apart, so that, when such distance is reached, the lock clamp 59 will engage top surface of the upper bracket 35, for example, preventing any further rotation of the rod by the patient that would tend to drive the brackets 33 and 35 further apart. This lock 59 may, if desired, be constructed so that it can only be moved or removed via the use of a special tool, so that is must otherwise remain in the precise location where the physical therapist has set it. For example, the two open ends may be linked to each other by a clamping screw which has a head designed to require a special tool to allow it to be tightened and loosened.

Referring back again to FIG. 5, in an alternative embodiment, the adjustment of the device 11 may be accomplished electronically (rather than manually). Accordingly, the gear box 51 is adapted to include at least one electric motor device 65, such as, for example, that shown in U.S. Pat. No. 5,651,764 incorporated herein by reference in its entirety, which would be employed to drive the miter gear 53 in either a clockwise or counterclockwise direction as well as stopping. Such an electric motor drive mechanism 65 may be operated by a hand-held or belt-supported finger-operated push-button controller (not shown) that might be connected through a wired and/or wireless electronic connection to a controller 67 mounted, for example, on the motor 65 or incorporated into a separate component (not shown). Alternatively, a voice-activated controller could alternatively be incorporated as a part of the motor drive. As discussed in greater detail below, the controller 67 mounted on the motor 65 may be adapted to store information relating to the duration of use, distraction, and degree of rotation. The controller 67 may also be programmable by a medical service provider so as to ensure that the patient complies with a particular traction therapy regimen.

Traction will gradually increase the spacing between a patient's vertebrae, and damaged cartilage and tissue between the vertebrae then may often swell to fill this space. When this occurs, should traction subsequently be removed too quickly, the swollen tissue between the vertebrae will often be pinched and cause severe pain. Thus, to avoid this potential problem, one should remove traction at a slow and comfortable rate. This is made possible by the unique design of coaxial lead screw surfaces that can be simultaneously and precisely rotated through miter gear drives conveniently accessible to the patient; or, alternatively, by a step-down mechanism in an electronically controlled device 11. This particular adjustment mechanism not only allows a patient to make a quick and easy reduction in the amount of traction to relieve nausea, should any unexpected difficulty be encountered when increasing traction, but also the beneficial combination of the miter gear arrangements with the pairs of coaxial lead screw surfaces facilitates, the release of traction at any time in a carefully controlled manner so the patient should be safe from tissue damage. Moreover, both symmetric and asymmetric traction are readily facilitated.

Because the device does not involve any shoulder girdle, chest harness or cranial fixation, the torso remains free, contributing to the portable/unencumbered nature of the device, while promoting a user-friendly design. The design of the device avoids any pressure on the mental process or chin, thus eliminating a potential physiologic reflex arc which might involve stimulation of the vagus nerve in the neck, the stimulation of which is often associated with unpleasant nausea and potentially dangerous heart rate reduction. In embodiments, where the device is molded of a plastic material, suitable plastic materials which are radiolucent can be chosen so that the user may continue wearing the brace even when undergoing radiographic studies, and in some instances, such a construction may also enhance the use of x-rays.

Rear Column Embodiment—

Figure 6:
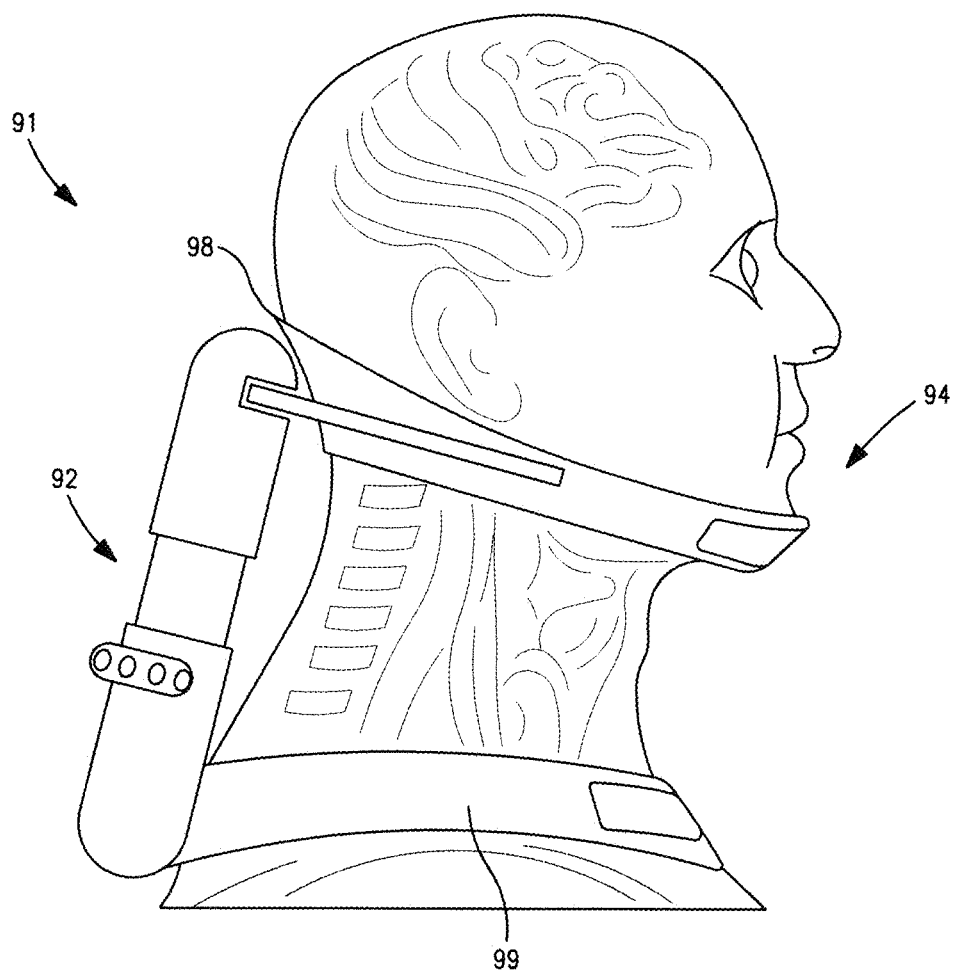
FIG. 6 is a side elevation view of a second exemplary embodiment of the traction 30 device according to the present invention disposed on a human subject.

FIG. 6 depicts a second exemplary embodiment of the traction device 91 of the present invention; the illustrated embodiment depicts the device 91 disposed on a human subject about the subject's neck. As illustrated, the device 91 generally comprises an adjustable single column support member 92 and a rotatable head brace 94. The traction device 91 provides cervical spinal bracing and/or traction by exerting stretching force between the shoulders and a head brace 94 that is in contact with the occipital region of the head and extends forwardly (anteriorly) to support the angle and body of the mandibulae on each lateral side of the head. Thus, while traction is applied, the user's head is fully supported.

Figure 6A:
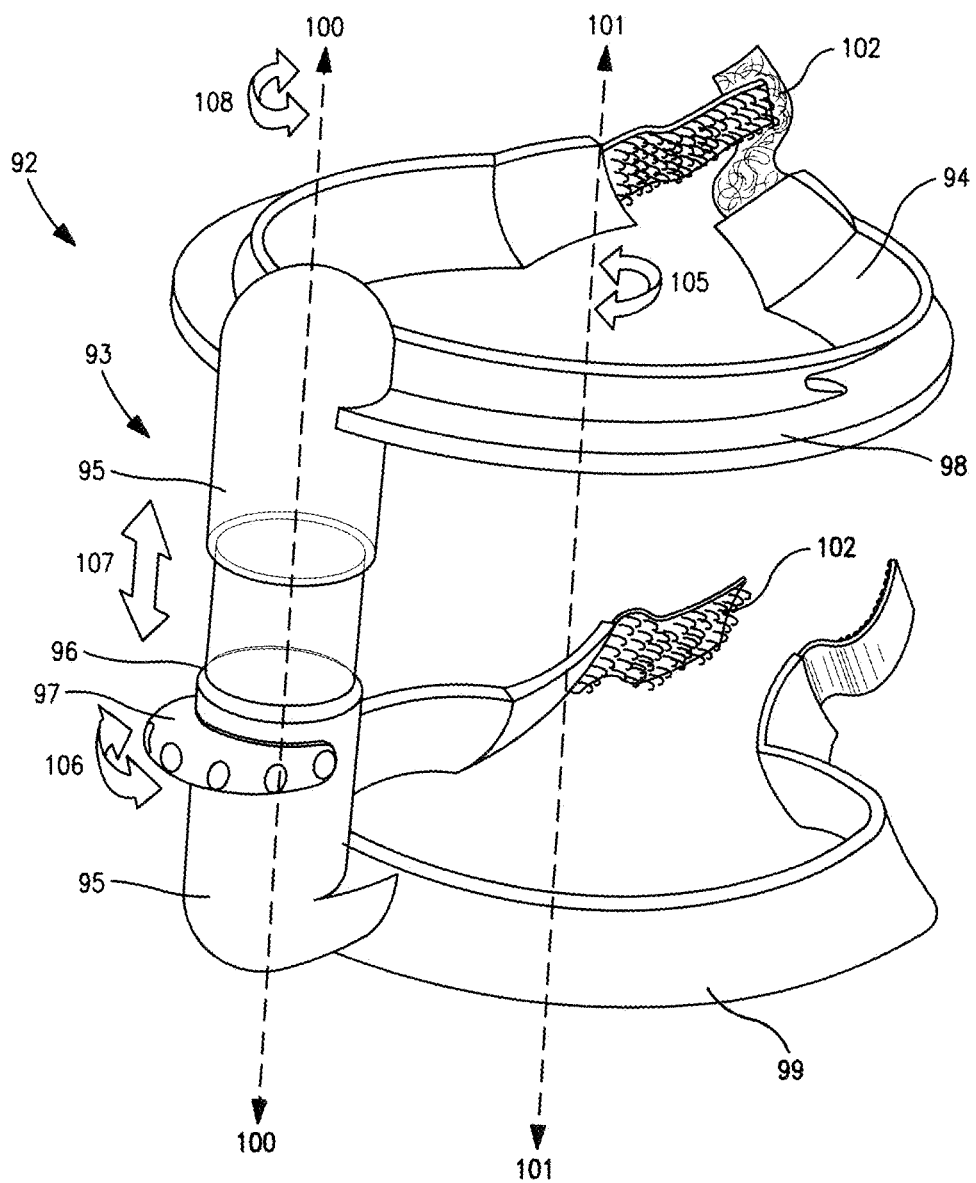
FIG. 6a is a rear perspective view of the traction device of FIG. 6, showing the advantageous axes of rotation of the present embodiment.

As illustrated by FIG. 6*a*, the head brace 94 of the present embodiment interacts with the upper circular structure 98 of the support member 92. The precise interaction will be discussed in detail below (see FIG. 6*c*).

Also illustrated in FIG. 6*a*, the support member 92 advantageously comprises an upper circular structure 98, a lower collar brace 99 and a single columnar, adjustable support 93. It is appreciated by the figure that both the head brace 94 and lower collar brace 99 of the present embodiment are forwardly opening. The ends of the open head brace 94 and collar brace 99 that terminate at the front openings are, in the illustrated embodiment, provided with inter-engaging Velcro straps 102. However, alternative fastening arrangements may be utilized consistent with the present invention so as to provide additional security and/or stability. Further, in one embodiment (not shown), the undersurface of the collar brace 99 (i.e. the portion which will come into contact with a wearer's shoulders) and/or the upper surface of the head brace 94 (Le. that portion which will come into contact with the wearer's neck and chin) are provided with padding or cushioning material. The padding or cushioning may be comprised of a conformable substance such as air, or memory foam pads. In an alternate embodiment, the shoulder portion of the collar brace 99 may be advantageously molded to the individual patient.

The columnar support 93 is disposed at the rear of the device 91 with regard to the subject's head; and further comprises an upper and lower sliding adjustment 95 and a central rod 96. The columnar support 93, as described, allows for the same functionality as the lateral side supports created by the overlapping walls 17, 19 of the collar member 15 of the previous embodiment (FIGS. 1 and 2). Specifically, the upper and lower sliding adjustments 95 are adapted to slide on the fixed central rod 96 in a superior and inferior direction, given by 107, with respect to the subject's head. The sliding adjustments 95 slide on the central rod 96 when the knob 97 is rotated in either direction given by 106; with one direction of rotation of the knob 97 being associated with the adjustments 95 moving closer together, and the other associated with the adjustments 95 moving farther apart. It is by this mechanism that traction is applied to the spine of a subject (or alternatively, traction is decreased).

As discussed above, the embodiment of FIGS. 6 and 6*a* may, instead of, or in conjunction with the turnable knob 97 advantageously comprise a small gearbox (not shown) such as that of the embodiments of FIGS. 1 and 2. Accordingly, the gearbox would be supported on the central rod 96 and would work with the internal mechanics of the columnar support member 93 to participate in and direct the sliding of the two sliding adjustments 95. In one further embodiment, the gearbox (not shown) would be electronically controlled by a control mechanism (not shown).

Referring back to FIG. 6*b*, the traction device 92 further comprises a lower collar brace 99. The lower collar brace 99 has a continuous curved undersurface, which is shaped and proportioned to lie comfortably on the shoulder girdle of the wearer at a location close to the base of the neck. It is constructed of material similar to that of the head brace 94 so as to preferably aesthetically resemble one another.

Figure 6B:
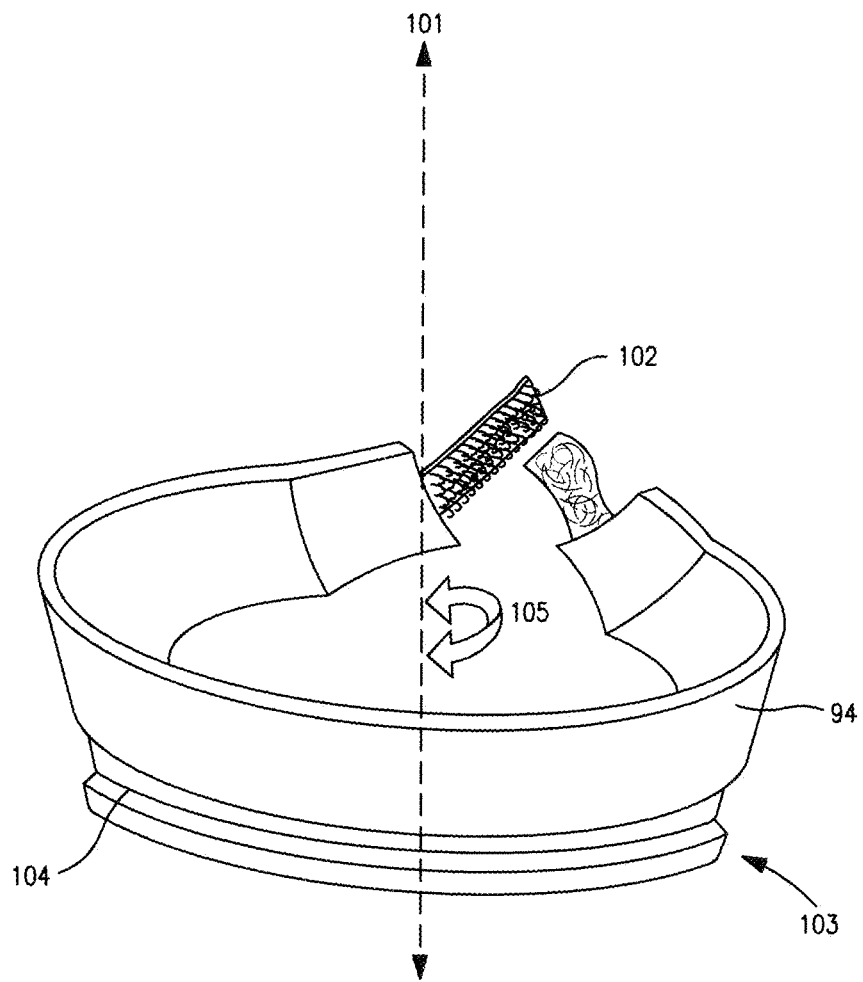
FIG. 6b is a perspective view of the head brace of the traction device of FIG. 6.
Figure 6C:
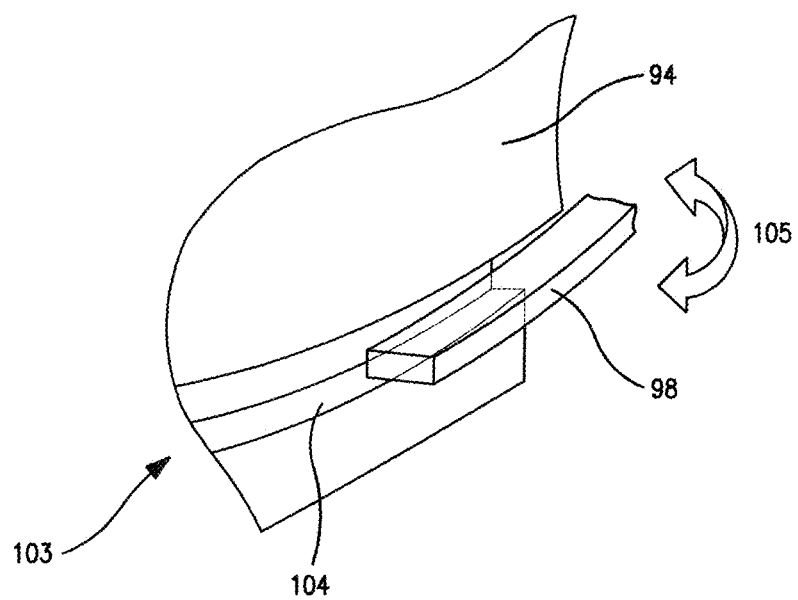
FIG. 6c is a cutaway perspective view of one embodiment of the traction feature of the exemplary traction device of FIG. 6.

Referring now to FIG. 6*b*, the head brace 94 of the present embodiment is shown. In the illustrated embodiment, the head brace 94 comprises a receiving feature 103 which is adapted to accommodate the upper circular structure 98 of the columnar support member 93. The interaction between the receiving feature 103 and circular structure 98 is best illustrated in FIG. 6*c*. Accordingly, the circular structure 98 of the columnar support member 93 rests on the landing 104 of the receiving feature 103. In a manner generally similar to that described with respect to FIG. 4 above, continuous and passive motion of the user's head is facilitated. The structure of the receiving feature 103 and circular structure 98 extending about the edge of the head brace 94 enables the user to move his/her head (e.g., rotate the head) in the direction given by 105 (generally left-to-right) about the axis 101. It is noted that the force of motion facilitated by the traction device 92 is generated by the user, no active mechanism or device is utilized to cause the head to rotate in this embodiment.

Referring back to FIG. 6*a*, in yet another embodiment, the traction device 92 is adapted to rotate about an axis 100 behind the wearer's head. Rotation about this axis 100 in the direction given by element 108 of FIG. 6*a* enables a wearer to move his head in a generally left-to-right direction as discussed with regard to rotation about axis 101 above; however, the axis of rotation is offset to a position directly behind the user's head/neck, which may have advantages in certain applications. Rotation about this axis 100 may be accomplished by providing, inter alia, an upper sliding adjustment 9S which is adapted to simultaneously rotate on the center rod 96 in the direction shown by element 108.

In yet another embodiment, the traction device 92 is adapted to permit rotation about both axes 100 and 101 so as to permit a wearer even greater range of motion of the head while distracted. Allowing the device to articulate or rotate around two axes 100, 101 permits in some cases a more comfortable user experience and greater range of motion than that produced by rotation about axis 100 or 101 alone. Rotation about these axes is accomplished by incorporating both the receiving feature 103 and circular structure 98 discussed in FIG. 6*b* as well as the rotating upper sliding adjustment 95 described above.

In another embodiment (not shown), the head brace 94 utilizes other mechanisms and features which enable the head brace 94 to rotate about the aforementioned axes while still maintaining an association with the upper circular structure 98 of the traction device 92, including utilization of roller bearings, ball bearings, fluid dynamic bearings, hydrostatic or gas bearings. In yet another embodiment, substantially frictionless rotation is better facilitated by the use of rare earth cobalt magnets of the type well known in the art. In one such variant, the repulsive magnetic force of such magnets is used to provide a standoff distance between two moving surfaces, thereby substantially eliminating a major source of friction in such a mechanism configured using more conventional mechanical solutions such as sliding surfaces.

It will be appreciated that while a single rear column is illustrated in the exemplary embodiment of FIG. 6, the invention is in no way so limited, and other numbers and columns of configurations may be used. For example, in one variant, two substantially parallel columns are used. Moreover, other non-columnar mechanisms may be used in place of the column illustrated in FIG. 6.

It may also be advantageous, in certain situations, for a physician or health care provider to be able to adjust the angular relationship of the head relative the shoulders of a wearer; i.e., the angle of the chin relative to the user's chest. However, as discussed above, his angular relationship generally must be completely fixed during the application of traction. Thus, in one embodiment of the present invention (see FIG. 6*d*), the device 92 comprises one or more lockable articulated joints or hinges 110, 113 fixedly attaching the various components of the traction device 92.

The first lockable joint or hinge 110 is adapted to attach the circular support structure 98 to the upper sliding adjustment 95. The joint 110 is placed in a manner which advantageously permits the circular structure 98 to rotate in the direction given by 111 while still being fixed to the upper sliding adjustment 95. In one embodiment, this is accomplished by utilization of interlocking, toothed faces which are set into mated cooperation with one another by a nut and bolt assembly and/or a wingnut 112 for increased torque (see FIG. 6*e* below). Myriad other approaches readily recognized by those of ordinary skill in the mechanical arts may be used as well for this function (i.e., locking the two components rigidly in a desired orientation).

When the head brace 94 is mated with the circular structure 98, the head brace is also able to tilt or rotate in the direction given by 111. Once the appropriate angular adjustment (via a healthcare provider's instruction for example) is accomplished, the joint at 110 will be locked into place.

The illustrated embodiment further (optionally) provides a second lockable articulated joint or hinge 113 which is adapted to fixedly attach the lower collar brace 99 to the columnar support 93. The placement of the second locking hinge 113 enables the lower collar brace 99 to tilt or rotate in the direction given by 114 while still being fixed to the lower sliding adjustment 95. Thus, when the traction device 92 is worn, the lower collar brace 99 advantageously adjusts to the particular slope of the shoulders and clavicle of the specific wearer. As above, once the lower collar brace 99 is placed comfortably on the wearer, the hinge or joint 113 may be locked into place. The locking hinge mechanism of this embodiment may advantageously comprise the same mechanism as described above with regard to the first hinge 110, or may comprise various other hinging or rotational joint mechanisms of the type known in the art.

Figure 6D:
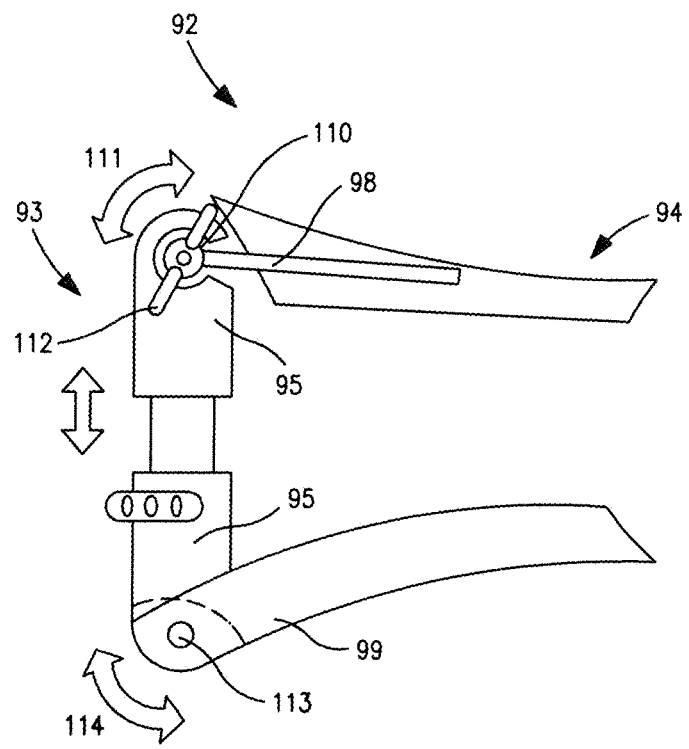
FIG. 6d is a side elevation view of an exemplary embodiment of the traction device of FIG. 6 adapted to permit adjustment of the angular relationship of the head of a wearer to the device.
Figure 6E:
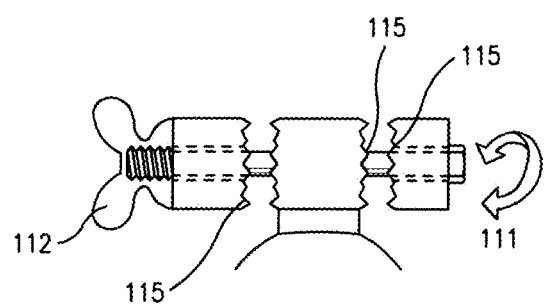
FIG. 6e is a side elevation view of an exemplary lockable hinging mechanism for use with the traction device of FIG. 6d.

FIG. 6*e* illustrates one embodiment of a hinging mechanism which may be utilized at hinges 110 and 113 of the embodiment of FIG. 6*d*. The figure illustrates the interface of the various toothed faces 115 and wingnut 112 assembly. As illustrated, the assembly permits a user to unscrew the wingnut 112 and rotate the circular support 98 in the direction given by 111. Then, to lock the components into place, the user will align the toothed faces 115 and re-screwed the wingnut 112 into the assembly. This embodiment has the advantage of not presetting large increments by which a user may increase or decrease tilt; the range of increments/positions is large based on the size and number of teeth on the toothed interfaces 115. Accordingly, locking the device 92 into a certain configuration is associated with a particular degree of angular adjustment of the head or shoulders with respect to the columnar support 93. Where it is known that a particular degree of adjustment is advantageous, the toothed interfaces 115 may be adapted to provide such degree as well as to inform the wearer the degree of angular adjustment at each stop along the interfaces 115.

In another embodiment (not shown), the hinging mechanism which may be utilized at hinges 110 and 113 of the embodiment of FIG. 6d comprises a push-button mechanism on the upper and/or lower sliding adjustment(s) 95. Pressing of the push-button mechanism releases a key or locking element which is adapted to fit and lock within one of a plurality of apertures disposed on the circular structure 98 and/or on the lower collar brace 99. The apertures are disposed, therefore, in a manner so as to facilitate step-wise increased or decreased tilting of 15 the head brace 94 and/or collar brace 99; and, as above, may be adapted to provide particular degrees of angular adjustment and inform the wearer of the degree associated with each aperture.

It is appreciated that various other mechanisms may be utilized consistent with the present invention to provide for the pivoting and/or hinging functions denoted by hinges 110, 113. It is further appreciated that other mechanisms may be employed to ensure that the sliding adjustments 95 will not function until the hinge(s) are locked into place, thus ensuring that a wearer is only able to apply traction once the angle is set; thus ensuring that a wearer will not be hurt or will not misuse the traction device.

Electronic Monitoring—

Figure 7:
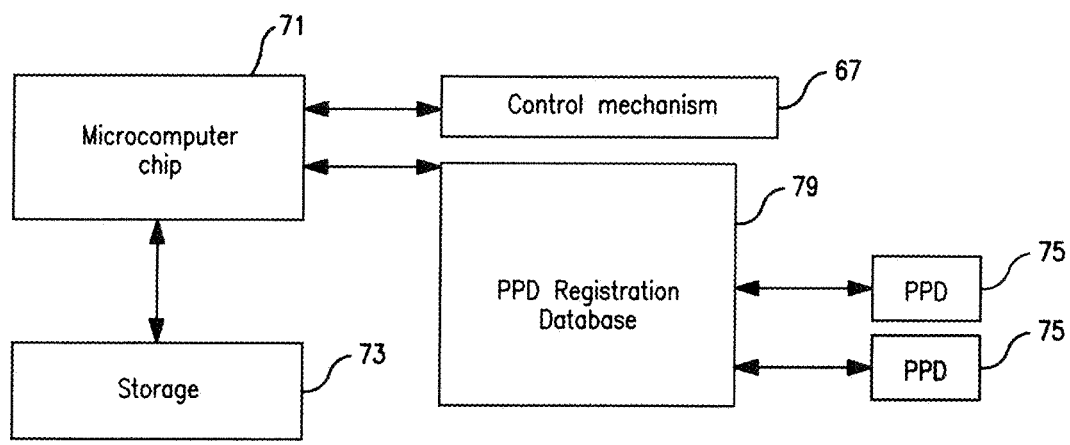
FIG. 7 is functional block diagram illustrating an exemplary electronics architecture according to the invention, including a microprocessor in communication with the control mechanism and patient/physician device.

Another salient aspect of the invention regards the ability of the device 11, 92 to electronically monitor certain facets of its use. As discussed above with respect to FIGS. 5 and 6A, in one embodiment the present invention is adapted to incorporate a control mechanism 67 adapted to control an electronic motor device 65. The device 11, 92 may also incorporate an array of sensors within and/or on the device 11, 92. Among these sensors may be at least one accelerometer and at least one force gauge, and a timer function. Referring to FIG. 7, the sensors are used as inputs to a microprocessor or micro controller 71 which can be programmed to read and measure the various signals from the sensors. The chip 71 may be physically located within or on the device 11, 92, or in an alternate embodiment, located remote to the traction device 11, 92.

The control mechanism 67 may further be in communication with the aforementioned microprocessor 71. The microprocessor 71 is then adapted to affect the functioning of the electronic motor 65 via the control mechanism 67 (see discussion below). Further, the microprocessor 71 may also be in communication with (and thereby controlled and/or monitored by) a patient and/or physician device (PPD) 75 (via a registration process, discussed below); such a device may comprise for example, a personal computer, PDA, laptop, web enabled telephone, etc. The communication between the microprocessor 71 and the electronic motor control mechanism 67 and/or the PPD 75 may be established via a wired connection, or through wireless means well known in the communications arts, including for example, Bluetooth, wireless LAN, etc.; other mechanisms for facilitating communication between the entities are also contemplated herein as well.

For security reasons, the microprocessor 71 will only be permitted to communicate with registered devices. Accordingly, a PPD registration database 79 is provided. Alternatively, encryption and authentication protocols can be used to effect such limited communications. In one embodiment, the database 79 is "small scale" and located at the traction device. It is appreciated, however, that the database may, in an alternative embodiment, be maintained at other locations and be "large scale" in nature. The "small scale" nature of the given database refers to the fact that the database will only be adapted to store identifying information about those PPD 75 registered to that traction device 11, 92; the identifying information may include, inter alia, IP address and the like. The "large scale" database would be adapted to store IP addresses and/or other identifying information of many traction devices, and of many registered patient and physician (or healthcare provider) devices PPD 75. The "large scale" database would therefore act as a central information hub.

In order to access traction data, input therapy program criteria, and/or receive reminders, updates and alarms, patients and health care providers must first establish a connection (either wired or wireless) to the database 79 and register their devices. Then, when the traction device 11, 92 has information to be sent (including an alarm, reminder or collected data), or when information is requested, those registered devices will receive the data. Further, the registered devices will be enabled to enter certain program criteria on an interface (discussed below) and have that criteria sent to the traction device's microprocessor 71 for implementation.

In one exemplary aspect, the microprocessor 71 comprises monitoring, transmission, and alert functionality, facilitated by various applications the microprocessor 71 is adapted to run. In some embodiments, the microprocessor 71 will also have associated storage and/or RAM 73. The microprocessor 71 and storage and/or RAM 73 are fundamental in providing certain ones of device 11, 92 function. For example, in one embodiment, the microprocessor 71 and associated storage and/or RAM 73 are adapted to run an application which continuously or periodically records certain aspects of the traction device 11, 92 operation or operating conditions.

As discussed above, the microprocessor 71 and associated storage and/or RAM 73 may be adapted to run various programs which will impart various function to the traction device 11, 92. For example, in one embodiment, the microprocessor 71 and associated storage and/or RAM 73 are adapted to run an application which would record and store data relating to, inter alia, the duration of use, force of distraction, extent of distraction, and degree of rotation. This information may then be subsequently sent to a PPD 75 for physician and/or patient evaluation and analysis, such as via a user interface (e.g., display) on the PPD. Transmission of the collected data to the PPD 75 may be accomplished via wired or wireless connection thereto. In order to transmit data wirelessly, the various PPD 75 must be registered with a PPD registration database 79 as discussed above.

In another embodiment, the microprocessor 71 and associated storage and/or RAM 73 would be adapted to run an application which would cause a signal or alarm to detonate after a prescribed amount of time. This function would enable a patient to appreciate when sufficient time has passed between therapy sessions and prompt the patient to begin a new session. As with the above mentioned application, data regarding the patient's use of (or failure to use) the device may be transmitted to a PPD 75 for physician and/or patient evaluation and analysis. Further, the application may also be adapted to cause a telephone or email message to be sent to remind a patient and/or the observing physician that a sufficient time has passed between therapy sessions. The conveyance of the aforementioned messages may be accomplished via the same registration mechanism described above.

In yet another embodiment, the microprocessor 71 and associated storage and/or RAM 73 would be adapted to run a program which would present a user (preferably a physician, physical therapist, chiropractor, or other healthcare provider) with options so as to create a traction-based therapeutic treatment schedule. The user will be able to enter certain criteria regarding the treatment schedule including, inter alia, the overall duration of the treatment, the duration of each therapy session, the maximum degree of rotation permitted in each session, the maximum extent and force of distraction permitted in each session, the distance of traction for each session, etc. Entering a treatment schedule will be accomplished via an application running on the user's PPD 75. The exemplary program would, as discussed, prompt a user (healthcare provider) to enter criteria regarding the treatment schedule, enable the user to enter other data or criteria, and transmit the created program to the device microprocessor 71 via the registration mechanism discussed above. A user may thereby achieve long term treatment goals. Alternatively, the storage and/or RAM 73 may have stored pre-programmed therapy sessions which the user (either a patient or healthcare provider) may select and employ. Again, selection here being accomplished via an application running on the user's PPD 75 and selections transmitted via the previously discussed registration mechanism. The same alarm and reminder functions discussed above may be employed in this embodiment as well.

In addition, an input component may be utilized in some embodiments whereby the patient can input feedback with regards to pain and discomfort associated with the programmed therapy sessions. In this fashion, the observing physician can correlate higher degrees of discomfort and/or pain with various measured parameters (e.g. degree of movement/rotation, etc.). Accordingly, the observing physician and/or patient can modify the therapy session in accordance with objective and subjective observed parameters. The input component may be incorporated into the device 11, 92 itself or may be operated externally (via e.g. a web-based interface on a host computing device).

The microprocessor 71 and associated storage and/or RAM 73 may further be adapted to run a preventative stopping program. According to this application, the device 11, 92 may be set to have manually entered and/or pre-programmed maxima and minima for the aforementioned monitored aspects of use including without limitation, duration of use, degree of rotation, extent and force of distraction, etc. The application may be adapted to absolutely prevent the use of the device beyond the prescribed minimum and maximum by either being adapted to stop further rotation of the rod mechanism (in either direction) or by being adapted to trigger a signal or alarm when the prescribed levels are breached.

PPD Interface—

As discussed above, the PPD 75 of the present invention are adapted to receive and send information to and from the microprocessor 71 of the traction device 11, 92. Accordingly, the PPD 75 must be adapted to run one or more computer applications having the ability to read and display information from the traction device 11, 92 and to send information to a traction device 11, 92 in a form the microprocessor 71 of the traction device 11, 92 can understand.

Accordingly, the present invention appreciates a computer program running on the physician (or healthcare provider) PPD 75. This program will enable the healthcare provider to extract data from the device regarding• duration of use, force and extent of distraction, degree of rotation, etc. The program would also advantageously provide the healthcare provider with the ability to trend and plot collected data in order to better determine compliance with a prescribed protocol and overall progress of an individual patient. Likewise, the program will enable the healthcare provider to "program" the traction device 11, 92 by setting forth, e.g. certain maximum and/or minimum limitations which will be implemented by the device 11, 92 via the microprocessor 71 acting on the control mechanism 67 (which acts upon the electronic motor 65). As discussed above, the "program" entered by the physician may control the duration of use, force and extent of distraction, and/or degree of rotation. Failure of a patient to meet a minimum requirement and/or breach of a maximum requirement may result in the device sending an alarm or a (telephone or email) reminder, or the traction device 11, 92 may merely disallow that rotation, amount of time and/or force and extent of distraction. This information can be used by the healthcare professional to monitor the patient's progress and "compliance" with the specified therapy.

Another fundamental concept is that the patient will also be able to see or obtain data regarding time of use, extent or forces applied and/or movements. This information can be utilized by the patient to monitor the patient's own progress and "compliance" with the specified therapy.

Methods—

Figure 8:
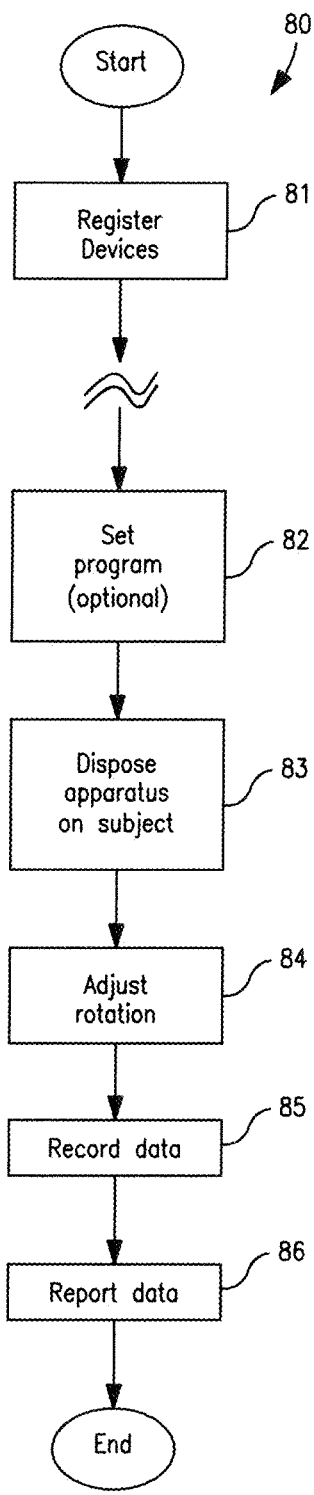
FIG. 8 is a logical flow diagram illustrating one exemplary method of using a traction device in accordance with the present invention.

An exemplary method 80 of using a traction device 11, 92 is given in FIG. 8. According to step 81 of the method, various PPD 75 are optionally registered to the PPD registration database 79. Next, per step 82, a program is optionally set. As discussed above, setting a program may comprise selecting a pre-programmed therapy schedule or manually entering program limitations for a single session or for a therapy schedule. Optionally, a user may operate the traction device 11, 92 without implementation of a program.

The traction apparatus 11, 92 is disposed on the subject at step 83. Per step 84, the traction of the device 11, 92 is adjusted. The traction may be manually adjusted via e.g. the starwheel 57 illustrated in FIG. 2, or turnable knob 97 of FIG. 6a, or may be adjusted electronically using an electronic motor (e.g., FIG. 5) via a programmed adjustment program transmitted from the microprocessor 71 to the control mechanism 67 which controls the motor 65.

Per step 85, data regarding various aspects the use of the device 11, 92 is recorded to the storage element 73 associated with the microprocessor 71. The same collected data is then reported to a PPD 75 via step 86. The data may then be reported by, inter alia, wireless transmission, copying of the data to a removable storage medium which will be placed in communication with a PPD 75, via a wired transmission, etc.

It will be recognized that while certain aspects of the invention are described in terms of a specific sequence of steps of a method, these descriptions are only illustrative of the broader methods of the invention, and may be modified as required by the particular application. Certain steps may be rendered unnecessary or optional under certain circumstances. Additionally, certain steps or functionality may be added to the disclosed embodiments, or the order of performance of two or more steps permuted. All such variations are considered to be encompassed within the invention disclosed and claimed herein.

While the above detailed description has shown, described, and pointed out novel features of the invention as applied to various embodiments, it will be understood that various omissions, substitutions, and changes in the form and details of the device or process illustrated may be made by those skilled in the art without departing from the invention. The foregoing description is of the best mode presently contemplated of carrying out the invention. This description is in no way meant to be limiting, but rather should be taken as illustrative of the general principles of the invention. The scope of the invention should be determined with reference to the claims.

What is claimed is:

1. A method of using a cervical spine brace and traction apparatus comprising:
   disposing a collar member of said traction apparatus on a collar region of a subject;
   mating a head member of said traction apparatus to said collar member in a substantially rotatable relationship, said substantially rotatable relationship comprising rotation only in a plane substantially transverse to a spinal column of said subject;
   adjusting a level of distraction of said traction apparatus, said adjusting said level of distraction comprising an electronic adjustment of said traction apparatus via an electronic control mechanism configured to control a motorized distraction adjustment mechanism;
   recording adjustment data relating to said traction apparatus;
   transmitting said adjustment data from said traction apparatus; and
   transmitting second data relating to input by said subject;
   based at least on said input, conducting a second adjusting of said level of distraction of said traction apparatus;
   wherein:
      said transmitting said adjustment data and said transmitting said second data comprise transmitting to a receiving device via a wired or wireless interface;
      said input comprises data representative of discomfort with a therapy session, said data representative of said discomfort with said therapy session comprising data representative of a level of discomfort experienced by said subject as part of said adjusting said level of distraction; and
      said receiving device comprises a computerized device authenticated via registration with a registration database.

2. The method of claim 1, further comprising executing at least one computer application configured to cause a microprocessor on said traction apparatus to receive and implement program criteria, said program criteria comprising at least one of:
   (i) maximum and/or minimum duration of use,
   (ii) maximum and/or minimum force of distraction,
   (iii) maximum and/or minimum extent of distraction, or
   (iv) maximum and/or minimum degree of rotation.

3. The method of claim 2, further comprising triggering an alarm or signal if said program criteria are not met, said alarm or signal comprising at least one of:
   illumination of a multi-colored LED light,
   an audible signal, or
   transmission of an electronic message to a remote apparatus.

4. The method of claim 1, wherein said mating said head member to said collar member comprises associating said head member and said collar member to at least one substantially adjustable support member, said at least one support member comprising at least one mechanism for moving said head member relative to said collar member so as to increase or decrease traction applied to said subject.

5. The method of claim 4, wherein said at least one substantially adjustable support member comprises a single substantially vertical beam.

6. The method of claim 1, wherein said recorded adjustment data comprises at least one of duration of use, degree of rotation, force of distraction, or extent of distraction.

* * * * *